(12) United States Patent
Hamilton et al.

(10) Patent No.: US 8,084,471 B2
(45) Date of Patent: Dec. 27, 2011

(54) PROTEOMIMETIC COMPOUNDS AS INHIBITORS OF THE INTERACTION OF NUCLEAR RECEPTOR WITH COACTIVATOR PEPTIDES

(75) Inventors: Andrew Hamilton, Guilford, CT (US); Jorge Becerril, Boston, MA (US)

(73) Assignee: Yale University, New Haven, CT (US)

( * ) Notice: Subject to any disclaimer, the term of this patent is extended or adjusted under 35 U.S.C. 154(b) by 212 days.

(21) Appl. No.: 12/226,369

(22) PCT Filed: Sep. 4, 2007

(86) PCT No.: PCT/US2007/019252
§ 371 (c)(1),
(2), (4) Date: Feb. 4, 2009

(87) PCT Pub. No.: WO2008/030408
PCT Pub. Date: Mar. 13, 2008

(65) Prior Publication Data
US 2009/0220586 A1    Sep. 3, 2009

Related U.S. Application Data

(60) Provisional application No. 60/842,615, filed on Sep. 5, 2006.

(51) Int. Cl.
*A01N 43/40*    (2006.01)
*A61K 31/44*    (2006.01)
*C07D 213/22*   (2006.01)

(52) U.S. Cl. ........................................ 514/333; 546/257

(58) Field of Classification Search .................. 546/257; 514/333
See application file for complete search history.

(56) References Cited

U.S. PATENT DOCUMENTS

| | | | | |
|---|---|---|---|---|
| 3,838,156 A | * | 9/1974 | Brundage et al. | 546/257 |
| 3,920,821 A | | 11/1975 | Schroder et al. | |
| 3,937,712 A | * | 2/1976 | Schroder et al. | 546/284.7 |
| 4,294,836 A | * | 10/1981 | Lesher et al. | 514/333 |
| 6,200,982 B1 | | 3/2001 | Collins et al. | |
| 6,410,729 B1 | * | 6/2002 | Spohr et al. | 544/320 |

FOREIGN PATENT DOCUMENTS

| | | | |
|---|---|---|---|
| DE | 2125310 | * | 11/1972 |
| DE | 229122 | * | 5/1992 |
| JP | 2001089452 | * | 4/2001 |

OTHER PUBLICATIONS

Ghozlan et al., Tetrahedron, 58(2002), pp. 9423-9429.*
Nantka-Namirski et al., Acta Poloniae Pharmaceutica (1977), 34(2), 133-8.*
Zayed et al., Journal of Heterocyclic Chemistry (1983), 20(1), 129-31.*
Attia et al., Acta Chimica Hungarica (1983), 112(1), 89-98.*
Shiao et al., Heterocycles (1990), 31(4), 637-41.*
Breast cancer research, Research page: a new class of drugs to treat breast cancer (2000), pp. 1-3.*
Abdelrahmani et al., Cardiovascular research (2005), vol. 65, pp. 772-781.*
Arany et al., Nature (2008), vol. 451, pp. 1008-1013.*

* cited by examiner

*Primary Examiner* — Janet Andres
*Assistant Examiner* — Niloofar Rahmani
(74) *Attorney, Agent, or Firm* — Henry D. Coleman; R. Neil Sudol; William J. Sapone

(57) ABSTRACT

The present invention relates to compounds, pharmaceutical compositions and methods which inhibit the binding of coactivator proteins in nuclear receptors, including estrogen receptors (alpha and/or beta), androgen receptors, thyroid receptors and peroxisome proliferators-activated receptors, among others. Compounds according to the present invention may be useful in the treatment of a variety of disease states or conditions which are mediated through nuclear receptors.

24 Claims, 6 Drawing Sheets

Figure 3
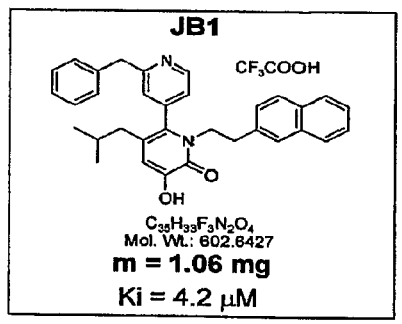
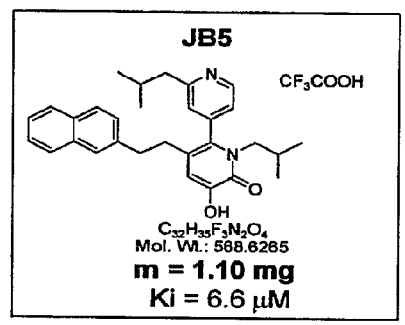
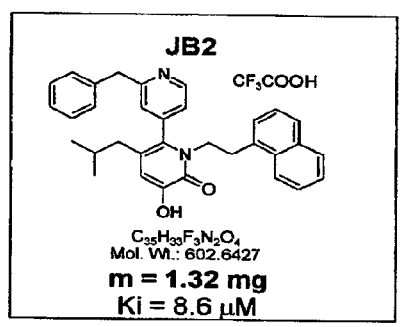
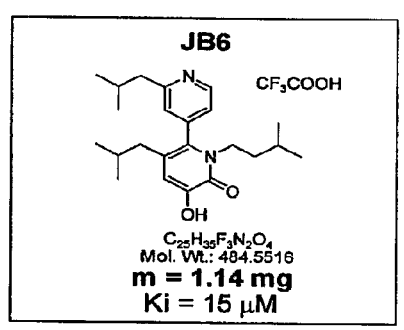
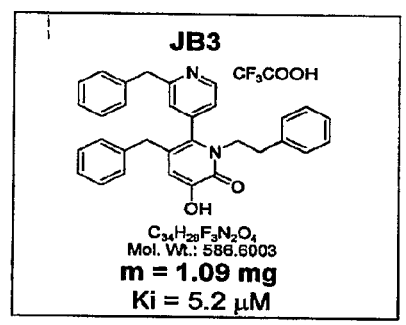
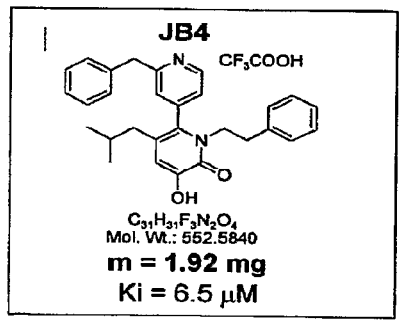

Figure 7

SAR Studies (Fluorescence Polarization Assay)

| Structure | $K_i$ (µM) |
|---|---|
| (pyridine-isobutyl-pyridone-CONH₂ with isopentyl) | >500 |
| (pyridine-isobutyl-pyridone-CONH₂ with isobutyl) | 127 |
| (pyridine-isobutyl-pyridone-COOH with isopentyl) | >500 |
| (pyridine-isobutyl-pyridone-CONH₂ with isopentyl, 5-Me-pyridine) | 328 |
| (pyridone-COOH with isopentyl, 5-Me-pyridine) | 208 |
| (pyridone-COOH with benzyl, pyridine-isobutyl) | 406 |

| Structure | $K_i$ (µM) |
|---|---|
| (pyridone-OCH₂COOH) | 110 |
| (pyridone-OCH₂CONH₂) | >500 |
| (pyridone-OCH₂COOH, 5-Me-pyridine) | 385 |
| (pyridone-OH, 5-Me-pyridine) | 15 |
| (pyridone-CONH₂, 5-Me-pyridine, isopentyl) | 161 |
| (pyridone-CONH₂, benzyl) | 173 |

Figure 8

SAR Studies II (Fluorescence Polarization Assay)

$K_i$ (μM):  15,  35,  >100,  >100

$K_i$ (μM):  >100,  6.5,  73,  >100

$K_i$ (μM):  23,  9.4,  >100,  4.3

Becerril J. and Hamilton A. *Submitted 2006*

PROTEOMIMETIC COMPOUNDS AS INHIBITORS OF THE INTERACTION OF NUCLEAR RECEPTOR WITH COACTIVATOR PEPTIDES

RELATED APPLICATIONS AND CLAIM OF PRIORITY

This application claims the benefit of priority of provisional application U.S. 60/842,615, entitled "Proteomimetics as Inhibitors of the Interaction of the Estrogen Receptor with Coactivator Peptides", filed Sep. 5, 2006, the entire contents of which is incorporated by reference herein.

FIELD OF THE INVENTION

The present invention relates to compounds, pharmaceutical compositions and methods which inhibit the interaction of coactivator peptides with nuclear receptors, including estrogen receptors (alpha and/or beta), androgen receptors, thyroid receptors and peroxisome proliferators-activated receptors, among others. Compounds according to the present invention may be useful in the treatment of a variety of disease states or conditions which are mediated through nuclear receptors.

BACKGROUND OF THE INVENTION

The estrogen receptor (ER) is a transcription factor that mediates the expression of estrogen-activated genes. The ER has been associated with a variety of diseases including breast cancer, osteoporosis and cardiovascular disease, and is therefore an important target for therapeutic intervention.[1] Binding of an estrogen molecule to the ligand binding domain (LBD) of the ER ultimately leads to interaction with specific DNA promoters and recruitment of coactivactor proteins. These coactivator proteins mediate the assembly of the transcriptional machinery and are therefore essential for expression of the ER-regulated genes. Traditionally, inhibition of the ER has been attempted by using antagonist molecules that bind to the LBD and trigger a conformational change that prevents the ER from recruiting the coactivator proteins.[2] An alternative and underexploited approach involves the small molecule inhibition of the interaction between the estrogen-activated ER and the coactivator proteins.[3a,b] Importantly, it has been shown that an analogous strategy can be used to target other nuclear receptors.[3c]

The coactivator proteins possess multiple copies of a conserved LXXLL motif also known as nuclear receptor box (where L is leucine and X is any amino acid). Extensive studies have shown that this short LXXLL sequence is important and sufficient for binding to the ER.[5] The X-ray structure of the ligand-bound ER and a fragment of the coactivator GRIP1 shows that the LXXLL peptide adopts an α-helical conformation where the leucine side chains in positions i and i+4 are projected into a hydrophobic groove on the ER surface while that in the i+3 position projects into a hydrophobic pocket.[4] Additionally, the crystal structure suggests that interactions between the coactivator peptide backbone and the charged residues that flank the binding groove on the ER further stabilize the complex.

In the search for inhibitors of this interaction, various short peptide derivatives based on the LXXLL sequence have been shown to disrupt the ER/coactivator interaction.[6] However, there have been only two reports of small molecule inhibitors with only one of them (with a $K_i$ value of 29 µM) designed to bind to this surface region of the ER and block the coactivator's approach.[3]

We have previously reported a broad strategy to the disruption of α-helix/protein interactions that involves the design of rigid scaffolds from which groups mimicking the surface functionality of an α-helix can be projected.[7] For example, 2,3',3"-trisubstituted terphenyls can mimic the i, i+4, and i+7 residues of two turns of an α-helix and lead to potent inhibitors of protein/helix contacts such as those between Bcl-xL/Bak and MDM2/p53.[8] In the case of the coactivator LXXLL motif, a modified approach is needed to incorporate the features of the i+3 leucine. We and others have shown that this can be simply achieved by placing a second ortho-substituent on a biaryl scaffold.[9] Separation of the elements of the i+3 side chain by a single methylene allows the adoption of a relative side chain conformation on the biaryl that closely mimics the distances and angular projections of the i, i+3, and i+4 groups of an α-helix.

BRIEF DESCRIPTION OF THE FIGURES

FIG. 3 shows additional compounds JB1-JB7 according to the present invention as well as their molecular weights, Ki values, etc.

FIGS. 7 and 8 show the results of a number of other compounds according to the present invention which were measured in the fluorescence polarization assay as described in the experimental section of the present application.

BRIEF DESCRIPTION OF THE INVENTION

Figure 1:
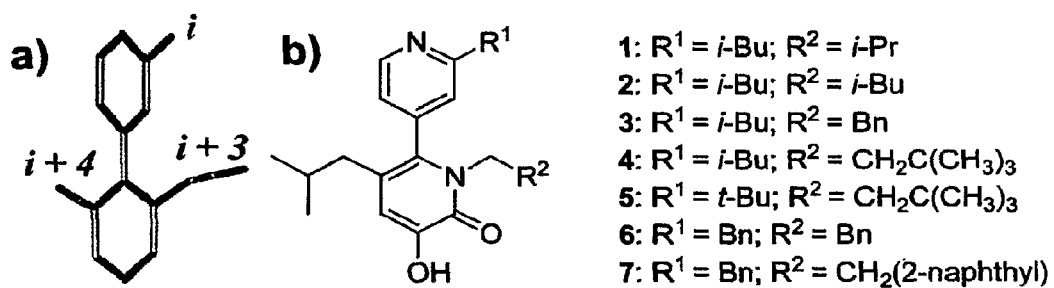
FIG. 1 shows a number of representative proteomimetic compounds according to the present invention. a) Shows the trisubstituted biaryl scaffold mimicking the i, i+3 and i+4 residues of an α-helix; b) Shows the structure of the pyridylpyridone derivatives 1-7.

The present invention relates to compounds according to the chemical structure:

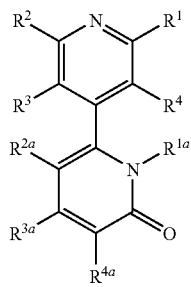

Where $R^1$ and $R^2$ are independently H, OH, a $C_1$-$C_8$ optionally substituted alkyl group, a $C_2$-$C_8$ optionally substituted alkene or alkyne group, an optionally substituted aryl or heteroaryl group, an optionally substituted heterocyclic group, a CN, $NO_2$, an optionally substituted $C_2$-$C_8$ carboxyl ester, an optionally substituted $C_2$-$C_8$ oxycarbonyl ester, an optionally substituted $C_2$-$C_8$ acyl, an optionally substituted $C_2$-$C_8$ thioester, an optionally substituted —$(CH_2)_n$—O—$(C_1$-$C_8)$ alkyl, an optionally substituted —$(CH_2)_n$—S—$(C_1$-$C_8)$alkyl, a —$(CH_2)_n NR^{N1}R^{N2}$ group or a —$(CH_2)_n C(O)$—$NR^{N1}R^{N2}$ group, wherein $R^{N1}$ and $R^{N2}$ are each independently H, an optionally substituted $C_1$-$C_6$ alkyl group (preferably optionally substituted with at least one hydroxyl group), an optionally substituted aryl group, an optionally substituted heteroaryl group or an optionally substituted heterocyclic group, or N forms an optionally substituted guanidino group with $R^{N1}R^{N2}$;

$R^3$ and $R^4$ are each independently H, OH, or an optionally substituted $C_1$-$C_3$ alkyl group (if substituted, preferably substituted with OH, or a halogen, preferably F), $COOR^E$ or a $COR^E$ group, where $R^E$ is H or a $C_1$-$C_3$ optionally substituted alkyl group;

$R^{1a}$ is H, $C_1$-$C_8$ optionally substituted alkyl group, a $C_2$-$C_8$ optionally substituted alkene or alkyne group, an optionally substituted aryl or heteroaryl group, an optionally substituted heterocyclic group, an optionally substituted $C_2$-$C_8$ carboxyl ester; an optionally substituted $C_2$-$C_8$ oxycarbonyl ester having at least one methylene group bridging the amine to the oxycarbonyl group, an optionally substituted $C_2$-$C_8$ acyl, an optionally substituted $C_2$-$C_8$ thioester, an optionally substituted —$(CH_2)_y$—O—$(C_1$-$C_8)$alkyl, an optionally substituted —$(CH_2)_y$—S—$(C_1$-$C_8)$alkyl, a —$(CH_2)_y NR^{N1}R^{N2}$ group or a —$(CH_2)_y C(O)$—$NR^{N1}R^{N2}$ group, wherein $R^{N1}$ and $R^{N2}$ are each independently H, an optionally substituted $C_1$-$C_6$ alkyl group (preferably optionally substituted with at least one hydroxyl group), an optionally substituted aryl group, an optionally substituted heteroaryl group or an optionally substituted heterocyclic group;

$R^{2a}$ is H, OH, a $C_1$-$C_8$ optionally substituted alkyl group, a $C_2$-$C_8$ optionally substituted alkene or alkyne group, an optionally substituted aryl or heteroaryl group, an optionally substituted heterocyclic group, a CN, $NO_2$, an optionally substituted $C_2$-$C_8$ acyl, an optionally substituted $C_2$-$C_8$ carboxyl ester; an optionally substituted $C_2$-$C_8$ oxycarbonyl ester, an optionally substituted $C_2$-$C_8$ thioester, an optionally substituted —$(CH_2)_n$—O—$(C_1$-$C_8)$alkyl, an optionally substituted —$(CH_2)_n$—S—$(C_1$-$C_8)$alkyl, a —$(CH_2)_n NR^{N1}R^{N2}$ group or a —$(CH_2)_n C(O)$—$NR^{N1}R^{N2}$ group, wherein $R^{N1}$ and $R^{N2}$ are each independently H, an optionally substituted $C_1$-$C_6$ alkyl group (preferably optionally substituted with at least one hydroxyl group), an optionally substituted aryl group, an optionally substituted heteroaryl group, an optionally substituted heterocyclic group, or N forms an optionally substituted guanidino group or a 5 or 6-membered heterocyclic ring with $R^{N1}R^{N2}$;

$R^{3a}$ and $R^{4a}$ are independently H, OH, a $C_1$-$C_8$ optionally substituted alkyl group, a $C_2$-$C_8$ optionally substituted alkene or alkyne group, an optionally substituted aryl or heteroaryl group, an optionally substituted heterocyclic group, a CN, $NO_2$, an optionally substituted $C_2$-$C_8$ acyl, an optionally substituted $C_2$-$C_8$ carboxyl ester; an optionally substituted $C_2$-$C_8$ oxycarbonyl ester, an optionally substituted $C_2$-$C_8$ thioester, an optionally substituted —$(CH_2)_n$—O—$(C_1$-$C_8)$alkyl, an optionally substituted —$(CH_2)_n$—S—$(C_1$-$C_8)$alkyl, a —$(CH_2)_n NR^{N1}R^{N2}$ group or a —$(CH_2)_n C(O)$—$NR^{N1}R^{N2}$ group, wherein $R^{N1}$ and $R^{N2}$ are each independently H, an optionally substituted $C_1$-$C_6$ alkyl group (preferably optionally substituted with at least one hydroxyl group), an optionally substituted aryl group, an optionally substituted heteroaryl group or an optionally substituted heterocyclic group, or N forms an optionally substituted guanidino group or a 5- or 6-membered heterocyclic group with $R^{N1}R^{N2}$;

n is 0, 1, 2, 3, 4, or 5; and y is 1, 2, 3, 4, or 5, or a pharmaceutically acceptable salt, hydrate or solvate thereof.

In preferred aspects of the invention, $R^1$ is H, an optionally substituted $C_3$-$C_5$ alkyl (preferably an unsubstituted $C_4$ alkyl group), an optionally substituted (preferably unsubstituted) benzyl or optionally substituted (preferably unsubstituted) alkylene (preferably ethylene) naphthyl; $R^2$ is H, an optionally substituted $C_3$-$C_5$ alkyl (preferably an unsubstituted $C_4$ alkyl group), an optionally substituted (preferably unsubstituted) benzyl or optionally substituted (preferably unsubstituted) —$(CH_2)_n$-naphthyl (n is 1 or 2, preferably 1), with the proviso that at least one of $R^1$ or $R^2$ is H, $R^3$ and $R^4$ are preferably H; preferably $R^{1a}$ and $R^{2a}$ are each independently an optionally substituted $C_3$-$C_6$ alkyl (preferably an unsubstituted $C_4$ or $C_5$ alkyl), an optionally substituted (preferably unsubstituted) $(CH_2)_n$-phenyl (n is 0, 1, 2 or 3) or optionally substituted (preferably unsubstituted) —$(CH_2)_n$-naphthyl (n is 1 or 2, preferably 2); $R^{3a}$ is preferably H; $R^{4a}$ is preferably H, OH, optionally substituted O—$(C_1$-$C_3)$ alkyl (preferably O—$C_1$ alkyl substituted with carboxylic acid or amide, preferably carboxamide, group), or a carboxamide (—$C(O)NH_2$) group.

Preferred compounds also include, those which are set forth in FIG. 1, FIG. 3, FIG. 7, FIG. 8 as well as the compounds

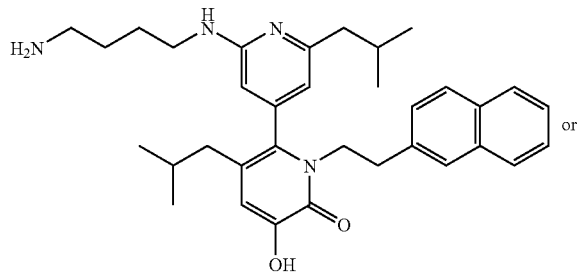

or

-continued

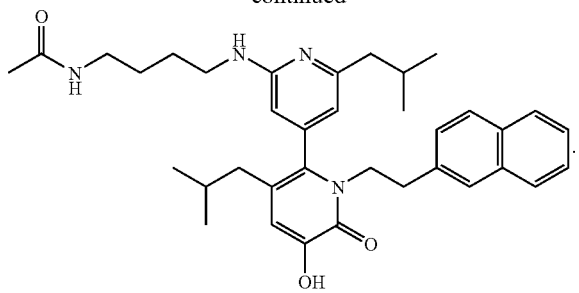

Compounds according to the present invention can be used to treat a number of disease states which are mediated through nuclear receptors, including estrogen receptors, androgen receptors, thyroid receptors and peroxisome proliferators-activated receptors, among others. These disease states or conditions include, for example, cancer (particularly breast, reproductive and other hormone-dependent cancers, leukemia, colon cancer, prostate cancer), reproductive and genito-urological diseases or conditions including endometreitis, prostatitis, polycystic ovarian syndrome, bladder control problems, hormone-related disorders, hearing disorders, cardiovascular disease and conditions including hot flashes and profuse sweating, hypertension, stroke, ischemia, myocardial infarction, obesity, osteoporosis, restoration of lipid profile, atherosclerosis, symptoms of menopause, inflammation, rheumatoid arthritis and osteoarthritis, hematologic diseases and conditions, including lymphoproliferative disorders, myeloproliferative disorders, eosinophilia, histiocytosis, paroxysmal nocturnal hemoglobinuria, and systemic mastocytosis, vascular diseases or conditions such as venous thrombosis, embolisms, among numerous others, disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine. Compounds according to the present invention may also be used to provide contraceptive compositions to prevent or reduce the likelihood of pregnancy after intercourse.

While not being limited by way of theory, it is believed that the present compounds exhibit activity in treating the above-described disease states and conditions by binding to the nuclear receptor surface, thus displacing coactivator peptides/proteins of nuclear receptors which are necessary for maximal receptor transcriptional activity, for example, estrogen (alpha and beta) receptors, androgen receptors, thyroid receptors and peroxisome proliferators-activated receptors, among others, resulting in inhibition of the expression mediated by the specific nuclear receptor and amelioration of the disease or condition which is mediated through that receptor.

In an alternative aspect, the present invention is directed to pharmaceutical compositions comprising an effective amount of at least one compound according to the present invention in combination with a pharmaceutically acceptable carrier, additive or excipient.

In still other aspects of the invention, a method comprises administering to a patient in need thereof an effective amount of one or more compounds according to the present invention in order to favorably influence or treat a disease state or condition which is mediated through a nuclear receptor, especially an estrogen alpha and/or beta receptor, androgen receptors, thyroid receptors and peroxisome proliferators-activated receptors, among others. These disease states or conditions include those which are set forth above.

In yet another aspect of the invention, a method for inhibiting peptide coactivators (such term especially including protein coactivators) of nuclear receptors from activating a nuclear receptor, namely estrogen (alpha and/or beta) receptors, androgen receptors, thyroid receptors and peroxisome proliferators-activated receptors, among others, comprises exposing a nuclear receptor in the presence of peptide coactivators to at least one compound according to the present invention to inhibit said peptide coactivator from binding to the nuclear receptor. Preferably, this inhibition occurs in vivo, in a patient in need thereof.

DETAILED DESCRIPTION OF THE INVENTION

The following definitions are used to describe the present invention. In instances where a term is not provided with a definition herein, that term is given its common meaning as used in context by those of ordinary skill in the art.

The term "patient" refers to a mammal, preferably a human, in need of treatment or therapy to which compounds according to the present invention are administered in order to treat or resolve a condition or disease state modulated through an estrogen notably, an estrogen receptor alpha (ERα) and/or beta (ERβ).

The term "modulate" means, to influence disease states or conditions, either through direct or indirect binding to a nuclear receptor and/or a peptide coactivator of a nuclear receptor, for example, a estrogen receptor alpha (ERα) and/or estrogen receptor beta (ERβ), an androgen receptor, a thyroid receptors and a peroxisome proliferators-activated receptors, among others which are improved by administering compounds according to the present invention, which preferably bind directly to the nuclear receptor or to coactivator peptides of the receptor (thereby inhibiting the expression of or their binding to the receptor) or by binding directly to the receptor to produce, either directly or indirectly, an improvement or lessening of a condition or disease state which was, prior to administration of a compound according to the present invention, suboptimal and in many cases, debilitating and even life threatening.

The term "nuclear receptor" refers to a receptor or class of proteins found within the interior of cells that are responsible for sensing the presence of hormones and certain other small molecules and which are coactivated (through facilitation and maximizing expression) by the presence of coactivator proteins containing an α-helical LXXLL motif. Hormone activated nuclear receptors work in concert with other proteins to increase the expression of specific genes. Nuclear receptors have the ability to directly bind to DNA and regulate the expression of adjacent genes, hence these receptors are classified as transcription factors. The regulation of gene expression by nuclear receptors is ligand dependent. In other words, nuclear receptors normally are only active in the presence of ligand (small molecule agonist or antagonist such as estradiol, among numerous others). The current view is that ligand binding alone to the nuclear receptor (although there is the possibility that the binding of a coactivator protein containing an α-helical LXXLL motif may influence events) results in a conformation change in the receptor which in turn activates the receptor resulting in up-regulation of gene expression.

A unique property of nuclear receptors which differentiate them from other classes of receptors is their ability to directly interact with and control the expression of genomic DNA. Consequently nuclear receptors play key roles in development and homeostasis of organisms. Nuclear receptors may be classified either according to mechanism or homology. In the present invention, nuclear receptors which are inhibited using compounds according to the present invention are those that need to bind coactivator proteins in order to present maximal transcriptional activity. The binding of agonist ligands to nuclear receptors induces a conformation of the receptor that preferentially binds coactivator proteins, whose main function is to help assemble the transcriptional machinery around the DNA sequence recognized by the nuclear receptor. These proteins have an intrinsic histone acetyltransferase (HAT) activity which weakens the association of histones to DNA, thereby facilitating access to the DNA for expression. In the case of the present invention, preferred embodiments inhibit the modulation of activity of the nuclear receptor by inhibiting the binding of protein activators which contain an α-helical LXXLL motif or its equivalent to the nuclear receptor of interest.

Exemplary nuclear receptors which are relevant to the present invention include, for example, estrogen receptors (alpha and/or beta), androgen receptors, thyroid receptors and peroxisome proliferators-activated receptors, among others.

The term "compound", as used herein, unless otherwise indicated, refers to any specific chemical compound disclosed herein and includes in context, tautomers, regioisomers (especially cis/trans), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., cis and trans isomers) and all optical isomers of the present compounds (e.g., R and S enantiomers), as well as racemic, diastereomeric and/or other mixtures of such isomers, as well as all pharmaceutically acceptable salt forms, solvates, polymorphs and prodrug forms of the present compounds, where applicable.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The term "cancer" includes any cancer of any origin and is used to describe all cancerous disease states and embraces or encompasses the pathological process associated with malignant hematogenous, ascitic, and solid tumors. The term "cancer" and the term "tumor" used in this application is interchangeable with the term "neoplasia".

Cancer which may be treated using compositions according to the present invention include, for example, cancers of the stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, melanoma, acute leukemia, including lymphocytic leukemia, hairy cell leukemia, and acute myelogenous leukemia, Ewing's sarcoma, small cell lung cancer, choriocarcinoma, rhabdomyosarcoma, Wilms' Tumor, neuroblastoma, mouth/pharynx, oesophagus, larynx, kidney, lymphoma, among others, and in particular, breast, reproductive, ovarian, cervical, uterine, endometrial and other hormone-dependent cancers. Drug-resistant cancers are also treatable using compounds according to the present invention and represent a preferred embodiment of the present invention.

The term "anti-cancer compound" or "anti-cancer agent" is used to describe any compound (including its derivatives) which may be used to treat cancer and is used in combination with one or more of the compounds according to the present invention in the treatment of cancer. The term "second anti-cancer compound", "second anti-cancer agent" or "additional anti-cancer compound" or "additional anti-cancer agent" may also apply to these agents in context. Anti-cancer agents as described hereunder are a subset of cytotoxic agents which may be used in the present invention in coadministration with compounds according to the present invention. Exemplary anti-cancer compounds for use in the present invention include anti-metabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anticancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox; dexrazoxane; docetaxel; doxorubicin; doxorubicin liposomal; Dromostanolone Propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. Note that one of ordinary skill in the art may readily employ any one or more of these second anti-cancer agents in combination with compounds according to the present invention to treat cancer.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., antiviral agent, antihyperproliferative disease agent, agents which treat chronic inflammatory disease, among others or as otherwise described herein), depending upon the desired therapeutic outcome and the disease state or condition treated.

The term "reproductive disorder" or "genito-urological disorder" is used to describe diseases or conditions of the genital or urinary tract and include such conditions as benign prostatic hyperplasia, prostatitis, infertility, polycystic ovarian syndrome, sexual dysfunction, endometritis, vaginal dryness, dyspareunia, as well as kidney and urinary complications, including bladder control, among others. Note that compounds/compositions according to the present invention also may be useful as contraceptive agents, i.e., agents which prevent or reduce the likelihood that a female will become pregnant after intercourse.

The term "hematologic disorder" is used to describe a disease or condition of blood and includes such diseases or conditions as lymphoproliferative disorders (diseases of white blood cells called T cells and B cells); myeloproliferative disorders (diseases in which too many of certain types of blood cells are made in the bone marrow); and includes four other blood disorders-eosinophilia, histiocytosis, paroxysmal nocturnal hemoglobinuria, and systemic mastocytosis, among others Hematologic disorders are distinguishable from leukemia, which is also treated using compounds according to the present invention.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substituent groups in compounds according to the present invention are as conventionally used in the art. Thus, the term alkylene aryl includes alkylene phenyl such as a benzyl group or ethylene phenyl or ethylene naphthyl group, alkylaryl, includes alkylphenyl such a phenyl group which has alkyl groups as substituents, etc.

"Aryl" refers to a substituted or unsubstituted monovalent aromatic radical having a single ring (e.g., benzene) or multiple condensed rings (e.g., naphthyl) and can be can be bound to compound according to the present invention at any position on the ring(s). Other examples of aryl groups include heterocyclic aromatic ring systems "heteroaryl" having one or more nitrogen, oxygen, or sulfur atoms in the ring, such as imidazole, furyl, pyrrole, pyridyl, indole and fused ring systems, among numerous others, which may be substituted or unsubstituted.

"Alkoxy" as used herein refers to an alkyl group bound through an ether linkage; that is, an "alkoxy" group may be represented as —O-alkyl where alkyl is as defined above. "Acyl" as used herein refers to an alkyl or other hydrocarbyl group bound through a keto linkage.

The term "cyclic", shall refer to a carbocyclic or heterocyclic group, preferably a 5- or 6-membered ring, but may include 4 and 7-membered rings or fused rings. "Bicyclic" or "bicyclo" refers to bicyclic The term "heterocycle" or "heterocyclic" shall mean an optionally substituted moiety which is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. Bicyclo groups are also contemplated for use herein. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated. In instances where a heterocyclic ring is fully unsaturated, there is overlap with the term "heteroaryl".

Exemplary heterocyclic groups (which term subsumes exemplary heteroaryl groups within context) which may be used in the present invention include for example, pyrrole, imidazole, diazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, ptridine, naphthyridine, quinoxaline, quinazoline, cinnoline, pyrrolopyridine, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, (−)carboline, acridine, phenazine, dibenzofuran, xanthene, dibenzothiophene, phenothiazine, phenoxazine, phenoxathiin, thianthrene, phenanthridine, phenanthroline, perimidine, pyridonaphthyridine, pyrazoloisoquinoline, pyrazolonaphthyridine, pyrimidoindole, indolizinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiopyene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole(oxadiazolidine), dihydrooxazone, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, tetrapyridonaphthyridine, tetrahydro-p-carboline, dihydroazepinoindole, hexahydroazepinoindole, tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, hexahydroindolizinoindole, dihydroindolobenzdiazepine, octahydroindoloquinolizine, hexahydroimidazopyridoindole, perhydrodibenzothiophene, tetrapyridonaphthyridine, tetrahydrocarboline, dihydroazepinoindole, hexahydroazepineindole, tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, hexahydroindolizinoindole, dihydroindolobenzdiazepine, octahydroindoloquinolizine, hexahydroimidazopyridoindole, hexahydropyrrolothiazepinoindole, dioxolane, dioxane, dithiolane, dithiane, dioxaindan, benzodioxane, chroman, benzodithiolane, benzodithiane, azaspiro[4.4]nonane, oxazaspiro[4.4]nonane, oxazaspiro[2.5]octane, dioxaspiro [4.4] nonane, azaspiro[4.5]decane, thiaspiro[4.5]decane, dithiaspiro[4.5]decane, dioxaspiro[4.5]decane, oxazaspiro [4.5] decane, azaspiro[5.5]undecane, oxaspiro[5.5]undecane, dioxaspiro[5.5]undecane, 2,3,4,9-tetrahydrospiro[P-carboline-1,P-cyclopentane], azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo [2.2.2] octane, diazabicyclo[2.2.2]octane, among others.

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 8 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl (carboxylic acid), oxygen (to form a keto group), $C_1$-$C_8$ alkoxy, CN, nitro, an optionally substituted amine (e.g. an alkyleneamine or a $C_1$-$C_6$ monoalkyl or dialkyl amine, which may be optionally hydroxyl substituted), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ thioether, amide (amido or carboxamido), substituted amide (especially mono- or di-alkylamide) or alkyleneamide, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various substituents may themselves be substituted with substituents as otherwise described herein. Various optionally substituted moieties may be substituted with 5 or more substituents, preferably no more than 3 substituents and preferably from 1 to 3 substituents. The term substituted may include, within context, substituents such as alkylene groups (represented as a —$(CH_2)_n$ or —$(CH_2)_y$ group where n is 0, 1, 2, 3, 4, or 5, preferably from 1 to 3 and y is 1, 2, 3, 4 or 5, preferably 1 to 3) which can bridge one moiety to a ring or other group on a pharmacophore or other moiety or substituent.

The term "hydrocarbon" or "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention all geometric isomers as mixtures (impure) or pure isomers are contemplated by the present invention. In preferred aspects, the present invention is directed to pure geometric isomers.

The term "optical isomer" is used to describe either of two kinds of optically active 3-dimensional isomers (stereoisomers). One kind is represented by mirror-image structures called enantiomers, which result from the presence of one or more asymmetric carbon atoms. The other kind is exemplified by diastereomers, which are not mirror images and which contain at least two asymmetric carbon atoms. Thus, such compounds have $2_n$ optical isomers, where n is the number of asymmetric carbon atoms. In the present invention all optical isomers in impure (e.g., as mixtures) or pure or substantially pure form (such as enantiomerically enriched or as separated diastereomers) are contemplated by the present invention. In certain aspects, the pure enantiomer or diastereomer is the preferred compound.

The present invention includes the compositions comprising the pharmaceutically acceptable salt, e.g., the acid or base addition salts of compounds of the present invention and their derivatives. The acids which may be used to prepare the pharmaceutically acceptable acid addition salts of the aforementioned base compounds useful in this invention are those which form non-toxic acid addition salts, e.g., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [e.g., 1,1'-methylene-bis-2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat disease states or conditions in patients or subjects who suffer from those conditions or disease states or are at risk for those conditions. In this method a compound in an effective amount is administered to a patient in need of therapy to treat the condition(s) or disease state(s). These disease states and conditions include, for example, cancer (particularly breast, reproductive and other hormone-dependent cancers, leukemia, colon cancer, prostate cancer), reproductive and genito-urological diseases or conditions including endometritis, prostatitis, polycystic ovarian syndrome, bladder control, hormone-related disorders, hearing disorders, cardiovascular disease and conditions including hot flashes and profuse sweating, hypertension, stroke, ischemia, myocardial infarction, obesity, osteoporosis, restoration of lipid profile, atherosclerosis, symptoms of menopause, inflammation, rheumatoid arthritis and osteoarthritis, hematologic diseases and conditions, including lymphoproliferative disorders, myeloproliferative disorders, eosinophilia, histiocytosis, paroxysmal nocturnal hemoglobinuria, and systemic mastocytosis, vascular diseases or conditions such as venous thrombosis, embolisms, among numerous others, disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine. In a contraceptive embodiment, the present compounds may also be used to prevent or reduce the likelihood that a woman will become pregnant after intercourse by administering to said women before or after intercourse an effective amount of one or more compounds according to the present invention.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods which are well known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation, intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Ophthalmic formulations, eye ointments, powders, and solutions are also contemplated as being within the scope of this invention.

Compounds/compositions according to the present invention are administered in amounts which are effective for treating a particular condition or disease state. The amount of active compound administered will be dependent upon the condition of the patient, the disease state or condition to be treated and the route of administration. The amount of active to be administered may vary from about 0.001 mg/kg/day to as much as 100 mg/kg/day or more of the patient, about 0.005 mg/kg/day to about 10 mg/kg/day, about 0.01 mg/kg/day to about 1 mg/kg/day or any amount which is considered effective within the context of the active compound's use. The compound may be given at a concentration and for a duration which is effective to treat the disease state or condition in the patient. Although compounds according to the present invention may be administered by virtually any route of administration, oral administration is preferred because of the ease of administration and the enhanced patient compliance which generally occurs with this route of administration.

Compounds according to the present invention may also be administered in a manner which reduces the likelihood that a condition or disease state will occur or worsen. In this method, a patient at risk that a condition or disease state will occur or will worsen is administered an effective amount of a compound according to the present invention to a patient at risk.

Chemical Synthesis

The general chemical methodology is represented by the synthesis of nuclear receptor, e.g. ER inhibitors, which is presented in scheme 1, which appears below. Synthesis of compounds according to the present invention proceeds through well known methods in the art.

In general, the reaction for compounds according to the present invention proceeds from a starting 4-functional pyridine derivative (which may utilize a cyano group or other moiety which can be later functionalized to form the 2-pyridone group to which the original pyridine compound is attached). Various pyridine compounds may be purchased commercially or synthesized using well known methods known in the art. After synthesizing the relevant substituted pyridine compound containing the appropriate functional groups (such as the indicated cyano group and other substituent), the functional group at the 4-position of the pyridine may be derivatized using standard chemical synthetic methods in the art to form the substituted 2-pyridone group at the 4 position of the original pyridine ring. Literally countless compounds may be readily synthesized using this conceptual approach.

By way of exemplary synthesis, a substituent may be introduced into the $R^1$ or $R^2$ position of the pyridine ring as indicated, or by other methods which are well know in the art. In appropriate instances, standard blocking or protecting groups may be used to inactivate an otherwise active functional group, allow a chemical reaction to occur and remove the blocking or protecting group to allow the underlying functional group to participate in a later reaction. Once the pyridine ring is synthesized, it may be derivatized at the 4-position by forming a substituted pyridone ring as indicated in scheme 1. Substituents may be incorporated into the pyridone ring either before or after the formation of the pyridone ring, depending upon the reactions to be carried out and the substituent to be incorporated. The method may be generally used to synthesize a huge number of compounds according to the present invention.

Scheme 1. Exemplary Synthesis of Compounds of the Present Invention

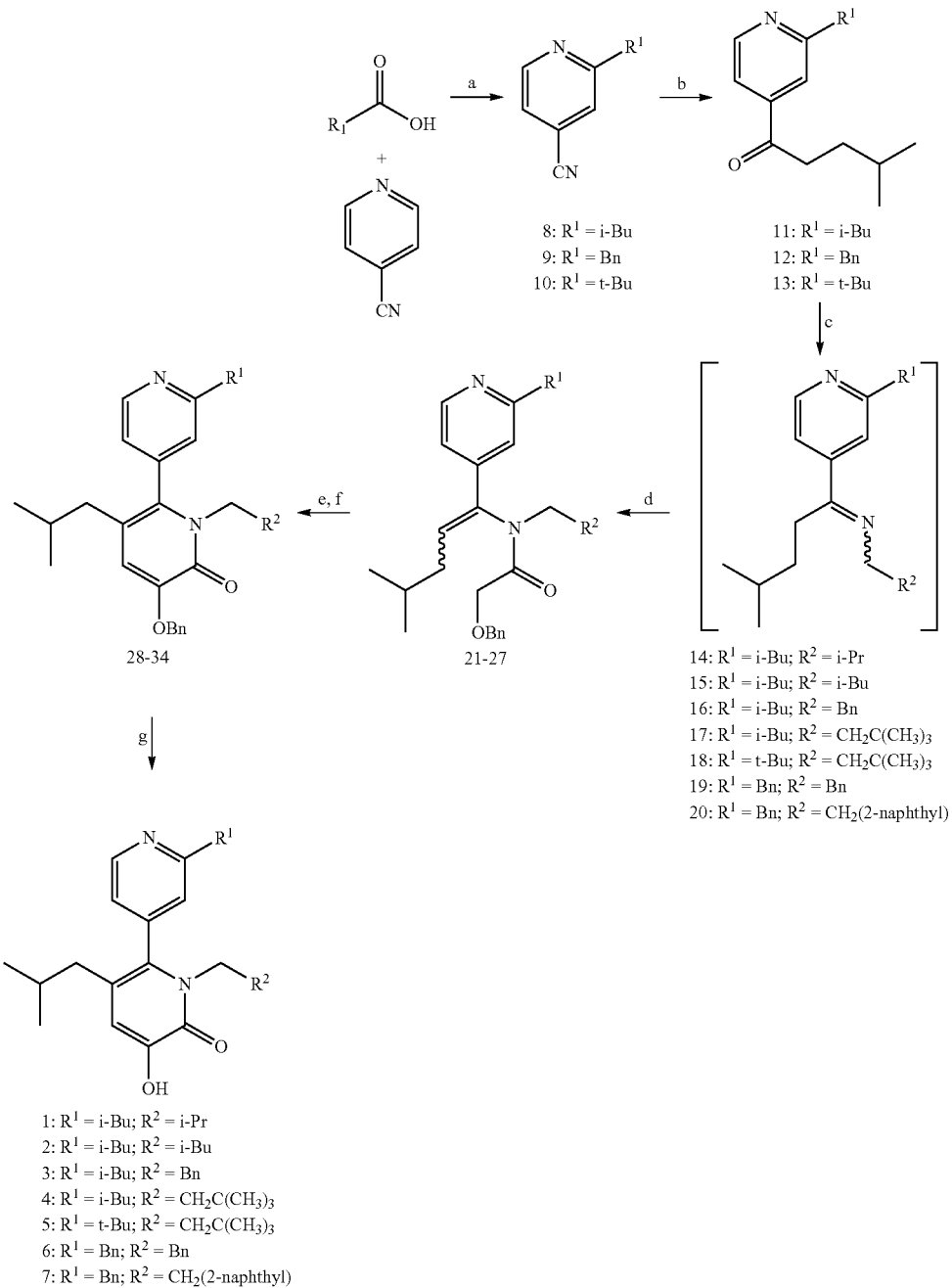

Reagents and conditions: (a) AgNO$_3$, (NH$_4$)$_2$S$_2$O$_8$, TFA, C$_6$H$_5$Cl, H$_2$O, 100° C.; (b) isopentylmagnesium bromide, Et$_2$O, reflux; (c) R$^2$CH$_2$NH$_2$, TiCl$_4$, CHCl$_3$, 23° C.; (d) benzyloxyacetyl chloride, CH$_2$Cl$_2$, 0° C.; (e) POCl$_3$, DMF, 70° C.; (f) NaOH, H$_2$O, 23° C.; (g) H$_2$, Pd—C, EtOAc, 23° C.

Methods of Treatment

Regardless of the mechanism, the compounds of the present invention may be used to treat disease states or conditions in patients or subjects who suffer from those conditions or disease states or are at risk for those conditions. In general, disease states or conditions which are mediated through nuclear receptors as otherwise described herein, in particular, the estrogen alpha or beta receptor, androgen receptors, thyroid receptors and peroxisome proliferators-activated receptors, among others, are treated using methods according to the present invention. In this method a compound in an effective amount is administered to a patient in need of therapy to treat the condition(s) or disease state(s). These disease states and conditions include, for example, cancer particularly breast, reproductive and other hormone-dependent cancers, leukemia, colon cancer, prostate cancer), reproductive and genito-urological diseases or conditions including endometreitis, prostatitis, polycystic ovarian syndrome, bladder control, hormone-related disorders, hearing disorders, cardiovascular disease and conditions including hot flashes and profuse sweating, hypertension, stroke, ischemia, myocardial infarction, obesity, osteoporosis, restoration of lipid profile, atherosclerosis, symptoms of menopause, inflammation, rheumatoid arthritis and osteoarthritis, hematologic diseases and conditions, including lymphoproliferative disorders, myeloproliferative disorders, eosinophilia, histiocytosis, paroxysmal nocturnal hemoglobinuria, and systemic mastocytosis, vascular diseases or conditions such as venous thrombosis, embolisms, among numerous others, disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine. In a contraceptive embodiment, the present compounds may also be used to prevent or reduce the likelihood that a woman will become pregnant after intercourse by administering to said women before or after intercourse an effective amount of one or more compounds according to the present invention.

In an alternative method, a compound according to the present invention is administered to a patient in an amount effective to inhibit the binding of a coactivator peptide to a nuclear receptor, in particular a nuclear receptor selected from the group consisting of an estrogen receptor (alpha and/or beta), an androgen receptor, a thyroid receptor and peroxisome proliferator-activated receptors, among others.

Rationale for Synthesis of Small Molecules

In the search for inhibitors of this interaction, various short peptide derivatives based on the LXXLL sequence have been shown to disrupt the ER/coactivator interaction.[6] However, there have been only two reports of small molecule inhibitors with only one of them (with a $K_i$ value of 29 µM) designed to bind to this surface region of the ER and block the coactivator's approach.[3]

We have previously reported a broad strategy to the disruption of α-helix/protein interactions that involves the design of rigid scaffolds from which groups mimicking the surface functionality of an α-helix can be projected.[7] For example, 2,3',3"-trisubstituted terphenyls can mimic the i, i+4, and i+7 residues of two turns of an α-helix and lead to potent inhibitors of protein/helix contacts such as those between Bcl-xL/Bak and MDM2/p53.[8] In the case of the coactivator LXXLL motif, a modified approach is needed to incorporate the features of the i+3 leucine. We and others have shown that this can be simply achieved by placing a second ortho-substituent on a biaryl scaffold.[9] Separation of the elements of the i+3 side chain by a single methylene (as in FIG. 2a) allows the adoption of a relative side chain conformation on the biaryl that closely mimics the distances and angular projections of the i, i+3, and i+4 groups of an α-helix.

In the present invention, there was synthesized a series of substituted pyridylpyridone derivatives shown in FIG. 1b, with the view that the bis-heteroaryl scaffold will have improved water solubility and bioavailability while allowing the ready introduction of substituents into the 2-pyridyl and 1,5-pyridone positions. Compounds 1-7 were synthesized via radical monoalkylation of p-cyanopyridine followed by addition of a Grignard reagent to obtain the alkylpyridylketone derivative.[10] Imine formation followed by reaction with benzyloxyacetyl chloride and subsequent cyclization yielded the appropriately substituted pyridylpyridone.[11]

Figure 9:
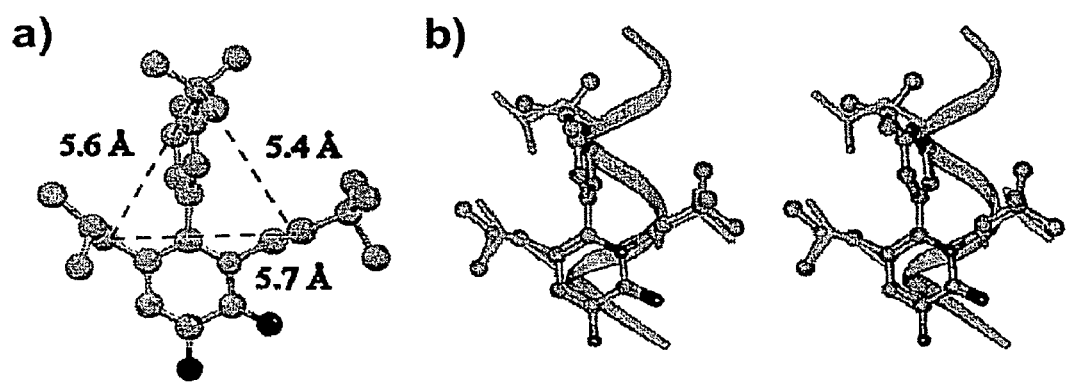
FIG. 9 shows the a) X-ray structure of compound 5; b) Stereoview of the X-ray structure of 5 superimposed to the α-helical LXXLL motif of GRIP1 peptide. Hydrogen atoms and non-relevant amino acid side chains have been omitted for clarity

The crystal structure of compound 5 evidences a non-planar conformation with an aryl-aryl dihedral angle of 82° and distances of 5.6, 5.4 and 5.7 Å between the atoms that mimic the β carbons of the key amino acid residues. These distances are similar to those found in α-helical LXXLL motifs. The α-carbon atoms of the i, i+3, and i+4 leucine residues of the GRIP1 peptide superimposed with the corresponding carbon atoms of 5 showed good matching with a rms deviation of 0.36 Å. This structure is presented in attached FIG. 9.

Biological Activity

To test the effectiveness of these derivatives in blocking the ER/coactivator interaction the present inventors used a fluorescent polarization (FP) assay based on rhodamine-labeled peptide D22 (Rho-LPYEGSLLLKLLRAPVEEV-COOH) which contains a single LXXLL motif.[5b] Displacement of this fluorescent peptide from the surface of estradiol-activated ER leads to a decrease of the polarization value. A control peptide that mirrors the second NR box of the coactivator protein SRC-1 (SRC-1 NR II) gave a $K_i$ of 0.95 µM (FIG. 2) which is comparable with the reported value of 1 µM.[3, 12]

Evaluation of the binding affinities of the pyridylpyridone compounds showed that most were able to inhibit the ER/coactivator interaction with low micromolar activity (Table 1, below). As expected, all the compounds were soluble under assay conditions. Compound 2 most closely mimics the LXXLL sequence and showed good binding with $K_i$=16 µM. Shortening of the i+3 mimicking N-alkyl side chain by one methylene as in 1, led to a 2-fold decrease in affinity supporting the conformational requirements for optimal i+3 and i+4 mimicry. Compounds 3 and 6 containing one and two benzyl groups in the i and i+3 positions were based on previously reported peptidomimetics and gave $K_i$ values of 9.4 and 6.5 µM, respectively.[6d] Introduction of a naphthyl group in 7 led to a further improvement with a $K_i$ value of 4.2 µM. Finally, steric constrains of the hydrophobic pockets on the ER could explain the weak affinity of 4 and 5 in which one or both of the i and the i+3 groups were converted to bulkier tert-butyl and neopentyl groups.

TABLE 1

Results of the fluorescence polarization assay.[a]

| Compound | $K_i$ (µm) | Compound | $K_i$ (µM) |
| --- | --- | --- | --- |
| SRC-1 NR II | 1.0 (0.3) | 4 | >50 |
| 1 | 34 (3) | 5 | >50 |
| 2 | 16 (3) | 6 | 6.5 (0.5) |
| 3 | 9.4 (2.0) | 7 | 4.2 (0.5) |

[a]Active compounds were tested in triplicate in at least three independent experiments. The values in brackets are the corresponding standard deviations.

Inhibition of coactivator binding by a small molecule involves either direct competition with the helical peptide for the ER surface or binding of the small molecule to the ligand binding site as an antagonist, deactivating the ER and preventing coactivator recruitment. To rule out the latter mechanism, a competitive radioligand assay with [$^3$H]estradiol was carried out to specifically measure the affinity of 3 for the estradiol binding site. According to the radioligand assay, 3 binds to this site with an affinity <0.001% the affinity of 17β-estradiol. Since the concentration of estradiol in the FP assays is kept constant at 2 µM, it was estimated that compound 3 should have a $K_i$ of 300 mM, six orders of magnitude higher than the $K_i$ found in the FP assay (9.4 µM). From this it was concluded that the helix mimetics prevent the coactivator association through direct competition for its binding site on the ER surface.

A new α-helix mimetic based on a pyridylpyridone scaffold was designed to mimic the surface functionality of an α-helical LXXLL motif Results from FP indicate that most compounds bind with $K_i$ values in the low micromolar range. The most potent inhibitors had comparable affinity to that of the control SRC-1 NR II; a peptide that mirrors the second LXXLL motif of the natural SRC-1 coactivator. Extensive SAR studies to improve the affinity of this scaffold as well as other structurally related molecules are undertaken.

Additional Studies

Figure 4:
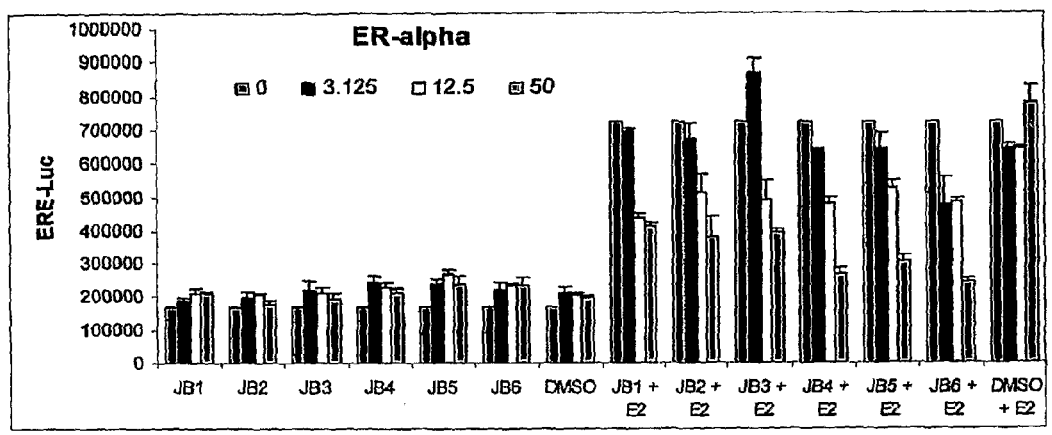
FIGS. 4-6 show the effect of the tested compounds (FIG. 3) on inhibition of estradiol-activated ER-alpha activity. All tested compounds seem to inhibit estradiol-activated ER-alpha activity to a similar extent while the vehicle (DMSO) has no significant effect (FIG. 4). The condition of the cells after overnight incubation with higher dosages of the compounds, was determined by measuring protein content (FIG. 5). All six compounds were found to decrease the total protein level in a dose-dependent manner. Such inhibition seems to be estradiol-independent. Normalization of the activity with the protein content reveals that all compounds activate the ERE activity to a certain extent, whereas they suppress estradiol-dependent ER-alpha activity (FIG. 6).
Figure 5:
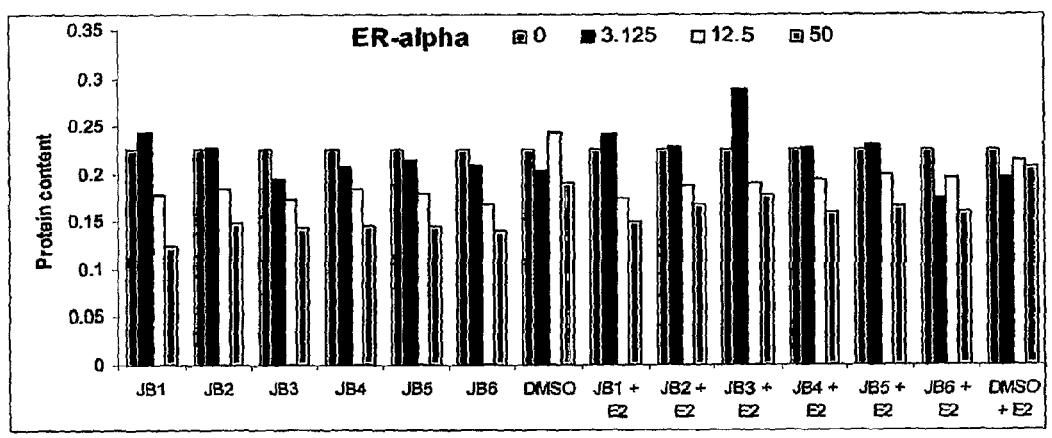
Figure 6:
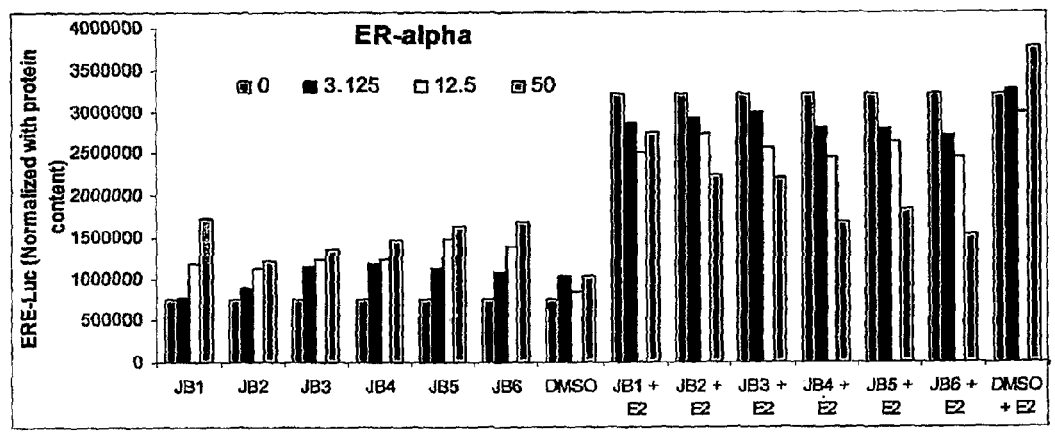

The present inventors also studied the effect of the compounds (JB1-JB6, FIG. 3) on estrogen receptor alpha-dependent transcription by using the breast cancer cells (MCF-7) stably transfected with ERE-Luc reporter gene. Cells were pretreated with the compounds for one hour prior to the incubation with or without estradiol (E2) for 20 hours. All tested compounds seem to inhibit estradiol-activated ER-alpha activity to a similar extent while the vehicle (DMSO) has no significant effect (FIG. 4). Since the condition of the cells was not good after overnight incubation with higher dosages of the compounds, protein content was also determined (FIG. 5). All six compounds were found to decrease the total protein level in a dose-dependent manner. Such inhibition seems to be estradiol-independent. Normalization of the activity with the protein content reveals that all compounds activate the ERE activity to a certain extent, whereas they suppress estradiol-dependent ER-alpha activity (FIG. 6). It appears that JB4, 5 and 6 are slightly more potent than the others while JB1 is the least potent. The data indicates that this class of compounds represents potential agonists of estrogen receptor alpha. They have some degree of estrogenic activity while they act antagonistically against estradiol.

EXAMPLES

General Methods. All chemicals were obtained from Sigma/Aldrich, Fluka and TCI America unless otherwise noted. TiCl$_4$ was distilled under vacuum before using. All air and/or moisture sensitive reactions were carried out under a positive pressure of nitrogen in flame-dried glassware. Solvents dimethylformamide (MF) and diethyl ether were obtained from commercial sources and dried on an Innovative Technology SPS-400 dry solvent system. Anhydrous chloroform was purchased from Sigma Aldrich. Column chromatography was performed using silica gel (230-400 mesh) from Solvent technologies. Thin layer chromatography was performed on Sigma Aldrich TLC Plates (silica gel on aluminum, 200 mm layer thickness, 2-25 mm particle size, 60 A pore size).

Analysis and purification by revere phase HPLC (rpHPLC) were performed using either a Waters 2487 dual λ UV detector with a Waters 1525EF binary pump using a Phenomenex Luna 5μ C18(2) 250×21 mm column run at 20 mL/minute (preparative), or a Waters 2487 dual λ UV detector with a Waters 1525 binary pump using a Microsorb-MV 300 Å C18 250×4.6 mm column run at 1 mL/minute (analytical), using gradient mixtures of water with 0.1% trifluoroacetic acid (TFA) (A) and 10:1 acetonitrile:water (B) with 0.1% TFA. Compound purity was confirmed by analytical rpHPLC using a linear gradient from 10% B to 100% B with changing solvent composition over 20 minutes. All gradients started after an initial 2 minutes of 100% A. Preparative HPLC purifications were performed using a linear gradient from 15% B to 100% B with changing solvent composition over 40 minutes. All gradients started after an initial 5 minutes of 100% A. Product fractions were always lyophilized to dryness. $^1$H NMR and $^{13}$C NMR spectra were recorded either on Bruker Avance DPX-500 or DPX-400 spectrometers at RT. Chemical shifts are expressed in parts per million using TMS as the internal standard. All high-resolution mass spectra (HRMS) were obtained from the Mass Spectrometry Laboratory at the University of Illinois at Urbana-Champaign on a Micromass Q-T of Ultima quadrupole time of flight mass spectrometer.

Purified ERα was purchased from Invitrogen. Fluorescent peptide D22 (Rhodamine-LPYEGSLLLKILLRAPVEEV) and Control peptide (CLTERHKILBRLLQE) (SRC-1 NR) were purchased from Keck Institute (Yale University; New Haven, Conn.) and further purified by reverse phase HPLC. Fluorescence polarization experiments were performed with an Analyst AD (Molecular Devices, Sunnyvale Calif.) spectrofluorimeter. The fluorescence polarization assays were performed using black 386-well plates purchased from Nalgen Nunc International.

Crystallographic Data

CCDC 636896 contains the supplementary crystallographic data for this paper. These data can be obtained free of charge from the Cambridge Crystallographic Data Center via www.ccdc.cam.ac.uk/data_request/cif

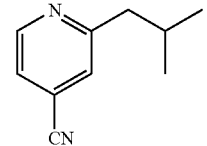

4-Cyano-2-isobutylpyridine (8)

p-cyanopyridine (8.00 g, 76.8 mmol) was added to a 1:1 mixture of chlorobenzene/water (1.5 L) in a 2 L round-bottom flask. Isovaleric acid (21.74 g, 212.8 mmol), (NH$_4$)$_2$S$_2$O$_8$ (34.40 g, 150.7 mmol), trifluoroacetic acid (8.78 g, 77.0 mmol) and AgNO$_3$ (1.040 g, 6.1 mmol) were added and the heterogeneous mixture was vigorously stirred and refluxed for 2 h. The reaction was cooled down to 0° C. and 8 M NaOH was added slowly until pH 9-10. The mixture was filtered through Celite and extracted with EtOAc (×3). The combined organic extracts were dried with MgSO$_4$ and the solvent removed in vacuo. The dark-brown oil was purified via flash chromatography (1:4 EtOAc/Hexane) to give a brown oil (6.538 g, 54%);

$^1$H NMR (400 MHz, CDCl$_3$): δ 0.95 (d, J=6.8 Hz, 6H), 2.13 (m, 1H), 2.73 (d, J=6.8 Hz, 2H), 2.37 (m, 2H), 8.73 (m, 1H); $^{13}$C NMR (100 MHz, CDCl$_3$): □ 22.3, 29.1, 47.3, 116.8, 120.4, 122.4, 125.0, 150.2, 163.3; HRMS-EI (m/z): [M+H$^+$] calcd for [C$_{10}$H$_{13}$N$_2$]$^+$, 161.1079. found, 161.1073.

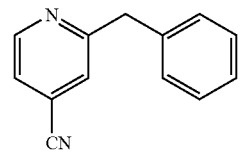

2-Benzyl-4-cyanopyridine (9)

p-cyanopyridine (4.00 g, 38.4 mmol) was added to a 1:1 mixture of chlorobenzene/water (750 mL) in a 1 L round-bottom flask. Phenylacetic acid (14.6 g, 107.5 mmol), (NH$_4$)$_2$S$_2$O$_8$ (17.1 g, 74.9 mmol), trifluoroacetic acid (4.38 g, 38.4 mmol) and AgNO$_3$ (0.510 g, 3.0 mmol) were added and the heterogeneous mixture was vigorously stirred at 50° C. for 2 h. The reaction was cooled down to 0° C. and 8 M NaOH was added slowly until pH 9-10. The mixture was filtered through Celite and extracted with EtOAc (×3). The combined organic extracts were dried with MgSO$_4$ and the solvent removed in vacuo. The dark-brown oil was purified via flash chromatography (1:5 EtOAc/Hexane) to give a brown oil (4.480 g, 61%); $^1$H NMR (400 MHz, CDCl$_3$): δ 4.19 (s, 2H), 7.23-7.35 (m, 7H), 8.68 (d, J=5.2 Hz, 1H); $^{13}$C NMR (100 MHz, CDCl$_3$): δ 44.4, 120.8, 122.7, 124.6, 126.9, 128.5, 128.9, 129.1, 137.9, 150.2, 162.7; HRMS-EI (m/z): [M+H$^+$] calcd for [C$_{13}$HN$_{11}$N$_2$]$^+$, 195.0922. found, 195.0917.

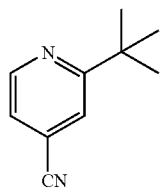

2-tert-Butyl-4-cyanopyridine (10)

p-cyanopyridine (4.00 g, 38.4 mmol) was added to a 1:1 mixture of chlorobenzene/water (750 mL) in a 1 L round-bottom flask. Trimethylacetic acid (10.88 g, 106-5 mmol), (NH$_4$)$_2$S$_2$O$_8$ (17.53 g, 76.8 mmol), trifluoroacetic acid (4.390 g, 38.5 mmol) and AgNO$_3$ (0.521 g, 3.1 mmol) were added and the heterogeneous mixture was vigorously stirred at 50° C. for 2 h. The reaction was cooled down to 0° C. and 8 M NaOH was added slowly until pH 9-10. The mixture was filtered through Celite and extracted with EtOAc (×3). The combined organic extracts were dried with MgSO$_4$ and the solvent removed in vacuo. The dark-brown oil was purified via flash chromatography (1:6 EtOAc/Hexane) to afford a brown solid (4.305 g, 70%); $^1$H NMR (400 MHz, CDCl$_3$): δ 1.39 (s, 9H), 7.38 (d, J=5.2 Hz, 1H), 7.63 (s, 1H), 8.73 (d, J=4.4 Hz, 1H); $^{13}$C NMR (100 MHz, CDCl$_3$): δ 29.2, 37.3, 116.4, 119.9, 120.4, 121.6, 149.1, 170.3; HRMS-EI (m/z): [M+H$^+$] calcd for [C$_{10}$H$_{13}$N$_2$]$^+$, 161.1079. found 161.1070.

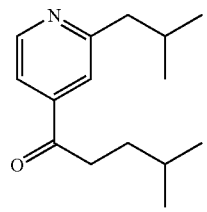

1-(2-Isobutyl-4-pyridyl)-4-methyl-pentanone (11)

Anhydrous Et$_2$O (30 mL) was added to magnesium turnings (1.114 g, 45.8 mmol) in a flame-dried flask. Addition of one drop of dibromoethylene was followed by slow addition of 1-bromo-3-methylbutane (5.895 g, 39.0 mmol) in 20 mL of anhydrous ether at a rate that kept the reaction mixture under reflux. Once the addition was completed the reaction was refluxed for 1 h and cooled to RT. The mixture was then added via cannula to a solution of 4-cyano-2-isobutylpyridine (3.000 g, 18.7 mmol) in 30 mL of anhydrous ether at 0° C. The mixture was stirred at RT for 30 min. and then refluxed for 3 h. The solution was cooled down to RT, poured into 200 mL of 0.5M HCl, and stirred for 30 min. A solution of 1M NaOH was added dropwise until the solution reached pH 9 and the resulting mixture was then extracted with ether (×3), dried with Na$_2$SO$_4$ and concentrated under vacuum. The resulting dark oil was purified by flash chromatography using 1:5 EtOAc/Hexane to give a brown oil (3.296 g, 75%); $^1$H NMR (400 MHz, CDCl$_3$): δ 0.94-0.98 (m, 12H), 1.61-1.66 (m, 3H), 2.15 (m, 1H), 2.75 (d, J=6.8 Hz, 2H), 2.97 (dd, J=7.2 Hz, J$_2$=7.6 Hz, 2H), 7.54 (m, 2H), 8.71 (d, J=4.8 Hz, 1H); C NMR (100 MHz, CDCl$_3$): δ 22.4, 27.7, 29.3, 32.7, 36.9, 47.6, 118.4, 120.7, 143.2, 150.3, 163.1, 200.3; HRMS-EI (m/z): [M+H$^+$] calcd for [C$_{15}$H$_{24}$NO]$^+$, 234.1858. found, 234.1856.

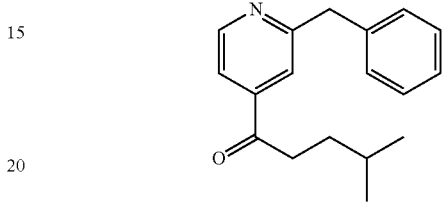

1-(2-Benzyl-4-pyridyl)-4-methyl-1-pentanone (12)

Anhydrous Et$_2$O (15 mL) was added to magnesium turnings (0.310 g, 12.8 mmol) in a flame-dried flask. Addition of one drop of dibromoethylene was followed by slow addition of 1-bromo-3-methylbutane (1.619 g, 10.7 mmol) in 10 mL of anhydrous Et$_2$O at a rate that kept the reaction mixture under reflux. Once the addition was completed the reaction was refluxed for 1 h and cooled to RT. The mixture was then added via cannula to a solution of 2-benzyl-4-cyanopyridine (1.000 g, 5.1 mmol) in 15 mL of anhydrous Et$_2$O at 0° C. The mixture was stirred at RT for 30 min. and then refluxed for 3 h. The solution was cooled down to RT, poured into 200 mL of 0.5M HCl, and stirred for 30 min. A solution of 1M NaOH was added dropwise until the solution reached pH 9 and the resulting mixture was then extracted with ether (×3), dried with Na$_2$SO$_4$ and concentrated under vacuum. The resulting dark oil was purified by flash chromatography using 1:4 EtOAc/Hexane to give a brown oil (0.801 g, 58%)

$^1$H NMR (400 MHz, CDCl$_3$): δ 0.91 (d, J=6.0 Hz, 6H), 1.58 (m, 1H), 2.88 (dd, J=7.6 Hz, J$_2$=6.8 Hz, 2H), 4.22 (s, 2H), 7.26-7.36 (m, 6H), 7.56 (m, 2H), 8.70 (d, J=4.8 Hz, 1H); $^{13}$C NMR (100 MHz, CDCl$_3$): δ 22.4, 27.7, 32.7, 36.9, 44.7, 118.8, 120.5, 126.6, 128.6, 129.0, 138.9, 143.6, 150.4, 162.4, 200.2; HRMS-EI (m/z): [M+H$^+$] calcd for [C$_{18}$H$_{22}$NO]$^+$, 268.1701. found, 268.1710.

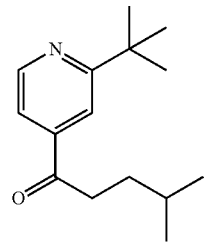

1-(2-tert-Butyl-4-pyridyl)-4-methyl-1-pentanone (13)

Anhydrous Et$_2$O (25 mL) was added to magnesium turnings (0.950 g, 39.1 mmol) in a flame-dried flask. Addition of one drop of dibromoethylene was followed by slow addition of 1-bromo-3-methylbutane (4.904 g, 32.5 mmol) in 15 mL of anhydrous ether at a rate that kept the reaction mixture under reflux. Once the addition was completed the reaction was refluxed for 1 h and cooled to RT. The mixture was then added via cannula to a solution of 2-tert-butyl-4-cyanopyridine (2.500 g, 15.6 mmol) in 30 mL of anhydrous ether at 0° C. The mixture was stirred at RT for 30 min. and then refluxed for 3 h. The solution was cooled down to RT, poured into 200 mL of 0.5M HCl, and stirred for 30 min. A solution of 1M NaOH was added dropwise until the solution reached pH 9 and the resulting mixture was then extracted with ether (×3), dried with $Na_2SO_4$ and concentrated under vacuum. The resulting dark oil was purified by flash chromatography using 1:6 EtOAc/Hexane to give a brown oil (3.296 g, 91%); $^1$H NMR (400 MHz, $CDCl_3$): δ 0.96 (d, J=6.4 Hz, 6H), 1.41 (s, 9H), 1.64 (m, 3H), 2.96 (t, J=7.6 Hz, 2), 7.52 (d, J=5.2 Hz, 1H), 7.78 (s, 1H), 8.73 (d, J=5.2 Hz, 1H); $^{13}$C NMR (100 MHz, $CDCl_3$): δ 22.4, 27.8, 30.1, 32.8, 37.0, 37.7, 116.4, 118.3, 143.3, 149.7, 170.9, 200.7; HRMS-EI (m/z): [M+H$^+$] calcd for $[C_{15}HN_{24}NO]^+$, 234.1858. found 234.1858.

General Procedure for the Synthesis of the Alkyl Pyridyl Imine Derivatives (14-19).

The corresponding pyridylketone derivative (1 equiv.) and alkylamine (4 equiv.) were dissolved in anhydrous chloroform (0.2 M) under $N_2$ and cooled in an ice-bath. Freshly distilled $TiCl_4$ (1.05 equiv.) was added dropwise over 10 min. and the reaction stirred for 30 min at 0° C. and overnight at RT. Diethyl ether was added and the suspension was stirred for 5 minutes until complete precipitation of $TiO_2$. The mixture was filtered through Celite and concentrated. Dry toluene (20 mL) was added and the solution was evaporated in vacuo. The addition/evaporation steps were repeated several times to ensure complete azeotropic removal of the excess of amine. The crude imine was confirmed by ESI-MS (Z/E isomers) and used in the next step without further purification (80-90% yield).

General Procedure for the Synthesis of the Enamide Derivatives (21-26).

The corresponding crude imine (1 equiv.) was dissolved in anhydrous $CH_2Cl_2$ (0.15 M) under $N_2$. The solution was cooled to 0° C. and benzyloxyacetyl chloride (1.05 equiv.) was added dropwise over 10 min as the reaction turned yellow. The mixture was stirred at 0° C. for 3 h. The solution was then poured into a saturated solution of $NaHCO_3$ and extracted with $CH_2Cl_2$ (×3). The combined organic extracts were washed with brine, dried with $MgSO_4$ and the solvent evaporated. The yellow oil was purified by flash chromatography (1:3 EtOAc/Hexane) to yield the corresponding enamide as an inseparable mixture of the Z/E diastereomers in approximately 70/30 ratio as concluded from $^1$H NMR spectra. The diastereomeric mixture was used in the next step without further separation (60-80%).

General Procedure for the Synthesis of the Pyridylpyridone Derivatives (28-33).

Dimethylformamide (3 equiv.) was added slowly to $POCl_3$ (5 equiv.) at 0° C. The mixture was stirred for 5 min., added to the corresponding enamide (1 equiv.) and stirred at 75° C. for 3 h. The viscous dark oil was taken up in 5 mL of THF and the solution poured into a mixture of ice and 30% NaOH solution (10 g ice in 50 mL of NaOH solution). The mixture was stirred vigorously for 3 h and then extracted with EtOAc (×2) and diethyl ether (×2). The combined organic layers were washed with water (×2), brine, dried with $Na_2SO_4$ and the solvent evaporated. The residue was purified by flash chromatography (10:25 EtOAc/Hexane) to obtain a viscous colorless oil.

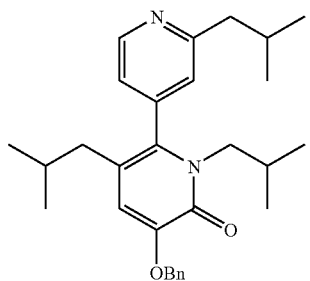

3-Benzyloxy-1,5-diisobutyl-6-(2-isobutyl-4-pyridyl)-1H-pyridin-2-one (28)

Yield 58%; $^1$H NMR (400 MHz, $CDCl_3$): δ 0.65 (d, J=6.8 Hz, 6H), 0.69 (d, J=6.8 Hz, 3H), 0.70 (d, J=6.8 Hz, 3H), 0.93 (m; 6H), 1.50 (m, 1H), 1.85-1.96 (m, 4H), 2.12 (m, 1H), 2.71 (d, J=7.2 Hz, 2H), 3.67 (m, 2H). 5.17 (s, 2H), 6.57 (s, 1H), 6.95 (m, 2H), 7.27-7.47 (m, 5H), 8.63 (d, J=4.4 Hz, 1H); $^{13}$C NMR (125 MHz, $CDCl_3$): δ 19.9, 20.0, 22.0, 22.1, 22.3, 22.4, 27.7, 29.2, 29.5, 40.4, 47.6, 52.8, 70.8, 116.1, 118.2, 122.8, 125.3, 127.5, 128.0, 128.5, 135.5, 136.4, 142.4, 147.6, 149.5, 158.0, 162.3; HRMS-EI (m/z): [M+H$^+$] calcd for $[C_{29}H_{39}N_2O_2]^+$, 447.3012. found, 447.3020.

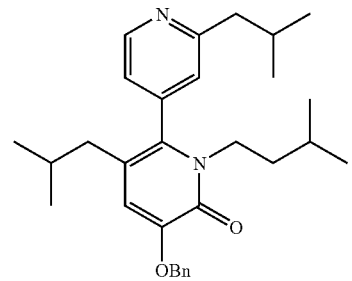

3-Benzyloxy-5-isobutyl-6-(2-isobutyl-4-pyridyl)-1-(3-methylbutyl)-1H-pyridin-2-one (29)

Yield 72%; $^1$H NMR (400 MHz, $CDCl_3$): δ 0.67-0.70 (m, 12H), 0.95 (t, J=6.0 Hz, 6H), 1.38-1.43 (m, 3H), 1.53 (m, 1H), 1.85 (d, J=7.2 Hz, 2H), 2.14 (m, 1H), 2.73 (dd, J=6.8 Hz, $J_2$=2.8, 2H), 3.72-3.76 (m, 2H), 5.15 (s, 2H), 6.58 (s, 1H), 7.00 (m, 2H), 7.30-7.48 (m, 5H), 8.66 (d, J=4.8 Hz, 1H); $^{13}$C NMR (100 MHz, $CDCl_3$): δ 22.98, 22.09, 22.12, 22.15, 22.29, 22.42, 26.2, 29.2, 29.4, 37.3, 40.3, 45.3, 47.5, 70.7, 116.0, 118.0, 122.3, 124.8, 127.4, 127.9, 128.5, 135.2, 136.4, 142.4, 147.5, 149.6, 157.3, 162.4; HRMS-EI (m/z): [M+H$^+$] calcd for $[C_{30}H_{41}N_2O_2]^+$, 461.3168. found, 461.3183.

27

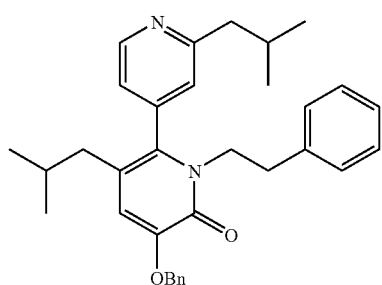

3-Benzyloxy-5-isobutyl-6-(2-isobutyl-4-pyridyl)-1-(2-phenylethyl)-1H-pyridin-2-one (30)

Yield 62%; $^1$H NMR (400 MHz, CDCl$_3$): δ 0.58 (m, 6H), 0.84 (d, J=5.2 Hz, 3H), 0.86 (d, J=5.2 Hz, 3H), 1.43 (m, 1H), 1.73 (m, 2H), 2.03 (m, 1H), 2.6-2.65 (m, 2H), 2.80 (m, 2H), 3.8 (t, J=6.0 Hz, 2H), 5.12 (s, 2H), 6.53 (s, 1H), 6.64-6.78 (m, 5H), 7.09-7.43 (m, 8H), 8.53 (d, J=4.0 Hz, 1H); $^{13}$C NMR (100 MHz, CDCl$_3$): δ 22.0, 22.1, 22.2, 22.4, 29.2, 29.3, 34.2, 40.3, 47.3, 48.4, 70.7, 116.0, 118.1, 122.3, 124.7, 126.5, 127.4, 128.0, 128.4, 128.5, 128.8, 135.3, 136.2, 138.1, 142.2, 147.5, 149.4, 157.4, 162.3; HRMS-EI (m/z): [M+H$^+$] calcd for [C$_{33}$H$_{39}$N$_2$O$_2$]$^+$, 495.3012. found, 495.3015.

28

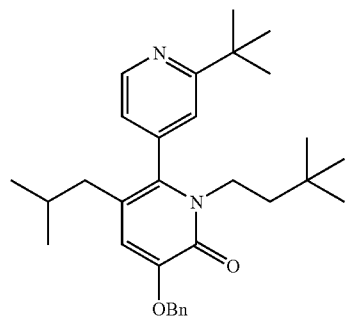

3-Benzyloxy-6-(2-tert-butyl-4-pyridyl)-5-isobutyl-1-(3,3-dimethylbutyl)1H-pyridin-2-one (32)

Yield 62%; $^1$H NMR (500 MHz, CDCl$_3$): δ 0.69 (m, 15H), 1.37-1.65 (m, 12H), 1.85 (m, 2H), 3.63 (m, 1H), 3.90 (m, 1H), 5.15 (s, 2H), 6.60 (s, 1H), 6.99 (d, J=5.0 Hz, 1H), 7.22-7.37 (m, 4H), 7.48 (d, J=7.5 Hz, 2H), 8.67 (d, J=7.5 Hz, 1H); $^{13}$C NMR (125 MHz, CDCl$_3$): δ 22.1, 22.2, 28.8, 29.4, 29.7, 30.1, 37.6, 40.3, 41.5, 43.4, 70.6, 116.0, 118.0, 120.9, 122.0, 127.4, 127.9, 128.5, 135.7, 136.4, 142.2, 147.4, 148.9, 157.3, 169.9; HRMS-EI (m/z): [M+H$^+$] calcd for [C$_{31}$H$_{43}$N$_2$O$_2$]$^+$, 475.3325. found 475.3324.

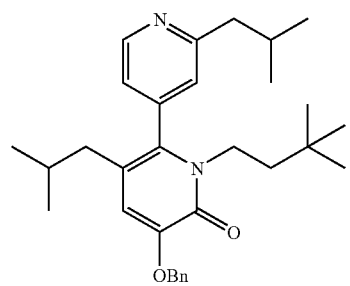

3-Benzyloxy-5-isobutyl-6-(2-isobutyl-4-pyridyl)-1-(3,3-dimethylbutyl)-1H-pyridin-2-one (31)

Yield 60%; $^1$H NMR (400 MHz, CDCl$_3$): δ 0.61 (m, 15H), 0.88 (m, 6H), 1.33 (m, 2H), 1.47 (m, 1H), 1.77 (d, J=7.6 Hz, 2H), 2.07 (m, 1H), 2.64 (m, 2H), 3.68 (m, 2H), 5.07 (s, 2H), 6.50 (s, 1H), 6.92 (m, 2H), 7.21-7.40 (m, 5H), 8.58 (d, J=4.8 Hz, 1H); $^{13}$C NMR (100 MHz, CDCl$_3$): δ 22.0, 22.1, 22.3, 22.5, 28.8, 29.2, 29.3, 29.4, 29.8, 40.4, 41.5, 43.5, 47.5, 70.7, 116.0, 118.0, 122.4, 124.9, 127.4, 127.9, 128.5, 135.3, 136.4, 142.3, 147.5, 149.5, 157.3, 162.4; HRMS-EI (m/z): [M+H$^+$] calcd for [C$_{31}$H$_{42}$N$_2$O$_2$]$^+$, 474.3246. found 474.3240.

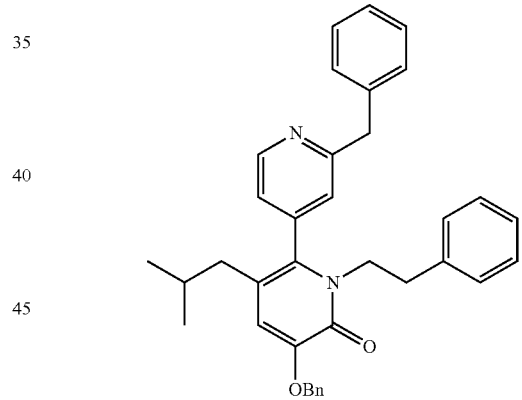

3-Benzyloxy-6-(2-benzyl-4-pyridyl)-5-isobutyl-1-(2-phenylethyl)-1H-pyridin-2-one (33)

Yield 55%; $^1$H NMR (400 MHz, CDCl$_3$): δ 0.56 (d, J=6.4 Hz, 3H), 0.62 (d, J=6.4 Hz, 3H), 1.42 (m, 1H), 1.72 (m, 2H), 2.80 (m, 2H), 3.79 (m, 1H), 3.90 (m, 1H), 4.19 (s, 2H), 5.2 (s, 2H), 6.56 (s, 1H), 6.71-6.79 (m, 4H), 7.15-7.49 (m, 13H), 8.61 (d, J=5.2 Hz, 1H); $^{13}$C NMR (100 MHz, CDCl$_3$): δ 22.0, 22.1, 29.2, 34.2, 40.3, 44.6, 48.5, 70.7, 116.0, 117.9, 122.6, 124.5, 126.5, 126.6, 127.4, 128.0, 128.5, 128.6, 128.8, 128.9, 129.0, 135.0, 136.2, 138.1, 138.9, 142.7, 147.5, 148.7, 157.3, 161.9; HRMS-EI (m/z): [M+H$^+$] calcd for [C$_{36}$H$_{37}$N$_2$O$_2$]$^+$, 529.2855. found 529.2858.

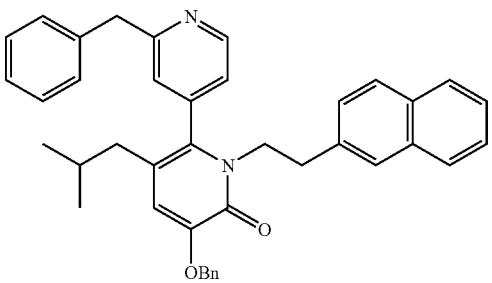

3-Benzyloxy-6-(2-benzyl-4-pyridyl)-5-isobutyl-1-(2-(2-naphthyl)ethyl)-1H-pyridin-2-one (34)

2-(2-naphthyl)ethylamine (3.940 g, 23.009 mmol) was added to a solution of 12 (1.342 g, 5.751 mmol) in 30 mL of anhydrous toluene under $N_2$ and the mixture was cooled to 0° C. in an ice-bath. Freshly distilled $TiCl_4$ (0.347 mL, 3.164 mmol) was added dropwise over 10 minutes and the reaction stirred for 30 minutes at room temperature. The mixture was then refluxed for 15 hours. Diethyl ether (100 mL) was added and the suspension was stirred for 3 hours after which the mixture was filtered through Celite and the solvent evaporated. Hexane (100 mL) was added and the mixture was kept in the fridge at 0° C. overnight. The mixture was then filtered through Celite and concentrated. The crude consisted of a Z/E mixture of the imine product 20 and the excess of non-volatile 2-(2-naphthyl)ethylamine. $^1$H-NMR spectroscopy was used to estimate the ratio and determine the number of equivalents of nucleophilic amine/imine. The mixture was dissolved in 20 mL of anhydrous $CH_2Cl_2$ under $N_2$. The solution was cooled to 0° C. and one equivalent of benzyloxyacetyl chloride per equivalent of amine/imine was added dropwise over 10 minutes. The mixture was stirred at 0° C. for 30 minutes and at room temperature overnight. The solution was poured into 50 mL of saturated solution of $NaHCO_3$ and extracted with $CH_2Cl_2$ (3×30 mL). The combined organic extracts were washed with brine, dried with $MgSO_4$, and the solvent evaporated. The residue was purified by flash chromatography (EtOAc/hexane 1:3→1:2) to yield the enamide 27 product as an inseparable mixture of the Z/E diastereomers in approximately 75/25 ratio as concluded from the $^1$H NMR spectrum. The diastereomeric mixture was used in the next reaction without further separation (2.205 g, 83% over two steps).

Dimethylformamide (0.95 mL, 12.32 mmol) was added slowly to $POCl_3$ (1.88 mL, 20.55 mmol) at 0° C. The mixture was stirred for 5 minutes, added to the enamide (2.200 g, 4.12 mmol) and stirred at 75° C. for 3 hours. The viscous dark oil was allowed to cool down to room temperature, taken up in 5 mL of THF and the solution poured into 100 mL of 30% NaOH solution. The mixture was stirred vigorously for 3 hours and then extracted with EtOAc (3×50 mL). The combined organic layers were washed with water (2×30 mL), brine (1×20 mL), dried with $MgSO_4$ and the solvent evaporated. The residue was purified by flash chromatography (EtOAc/hexane/$CH_2Cl_2$ 2:3:0.5) to obtain 34 as a white solid (1.053 g, 47% for the cyclization step). $^1$H NMR (500 MHz, $CDCl_3$): δ 0.55 (d, J=6.5 Hz, 3H), 0.62 (d, J=6.5 Hz, 3H), 1.41 (m, 1H), 1.67-1.79 (m, 2H), 3.00 (t, J=7.5 Hz, 2H), 3.90 (m, 1H), 4.04 (m, 2H), 4.15 (d, J=15.0 Hz, 1H), 5.22 (m, 2H), 6.60 (s, 1H), 6.63 (s, 1H), 6.77 (m, 1H), 6.94 (m, 1H), 7.15-7.47 (m, 11H), 7.52 (m, 2H), 7.68 (m, 2H), 7.81 (m, 1H), 8.61 (d, J=5.0 Hz, 1H); $^{13}$C NMR (125 MHz, $CDCl_3$): δ 22.4, 22.5, 29.6, 34.8, 40.7, 45.0, 48.9, 71.2, 116.5, 118.7, 122.9, 125.0, 126.0, 126.5, 127.0, 127.7, 127.9, 128.0, 128.4, 128.5, 129.0, 129.1, 129.3, 132.6, 133.9, 135.6, 136.1, 136.8, 139.4, 143.0, 148.0, 150.1, 157.9, 162.4; HRMS-EI (m/z): [M+H$^+$] calcd for $[C_{40}H_{39}N_2O_2]^+$, 579.3012. found 579.3008.

General Procedure for Benzyl Ether Cleavage (1-7)

The corresponding aryl benzyl ether (1 equiv.) was dissolved in ethyl acetate (approx. 0.03 M). Palladium on carbon (10% w/w) was added to the solution which was then hydrogenated for 3 h at RT and 1 atm of hydrogen. The mixture was filtered through Celite to obtain the corresponding product in 85-95% yield and high purity. The compounds were further purified for biological testing by preparative reverse-phase HPLC and lyophilized to afford the corresponding TFA salt.

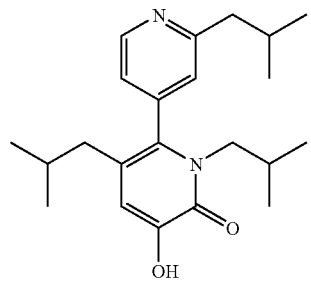

3-Hydroxy-1,5-diisobutyl-6-(2-isobutyl-4-pyridyl)-1H-pyridin-2-one (1)

$^1$H NMR (400 MHz, $CDCl_3$): δ 0.71 (m, 12H), 0.94 (d, J=6.8 Hz, 6H), 1.64 (m, 1H), 1.92 (m, 3H), 2.14 (m, 1H), 2.73 (d, J=7.2 Hz, 2H), 3.69 (m, 2H), 6.77 (s, 1H), 6.98 (m, 2H), 8.66 (d, J=4.8 Hz, 1H); $^{13}$C NMR (125 MHz, $CDCl_3$): δ 19.8, 19.9, 22.1, 22.2, 22.3, 27.8, 29.2, 29.5, 40.4, 47.5, 53.1, 115.7, 118.5, 123.0, 125.5, 133.4, 142.2, 145.7, 149.6, 158.4, 162.3; HRMS-EI (m/z): [M+H$^+$] calcd for $[C_{22}H_{33}N_2O_2]^+$, 357.2542. found, 357.2548.

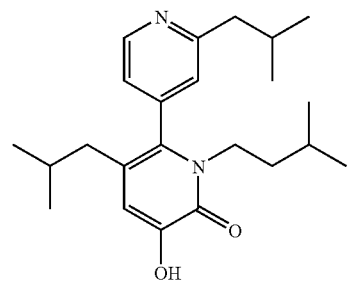

3-Hydroxy-5-isobutyl-6-(2-isobutyl-4-pyridyl)-1-(3-methylbutyl)-1H-pyridin-2-one (2)

$^1$H NMR (400 MHz, $CDCl_3$): δ 0.70 (m, 6H), 0.75 (m, 6H), 0.95 (d, J=6.8 Hz, 3H), 0.97 (d, J=6.8 Hz, 3H), 1.42 (m, 3H), 1.66 (m, 1H), 2.75 (m, 2H), 3.77 (m, 2H), 6.77 (s, 1H), 7.02 (m, 2H), 7.67 (s, OH), 8.68 (d, J=4.0 Hz, 1H); $^{13}$C NMR (100 MHz, $CDCl_3$): δ 22.0, 22.1, 22.18, 22.22, 22.3, 22.4, 26.2, 29.2, 29.4, 37.3, 40.4, 45.6, 47.5, 115.7, 118.4, 122.6, 125.2, 133.2, 142.2, 145.6, 149.6, 157.8, 162.5; HRMS-EI (m/z): [M+H$^+$] calcd for $[C_{23}H_{35}N_2O_2]^+$, 371.2699. found 371.2705.

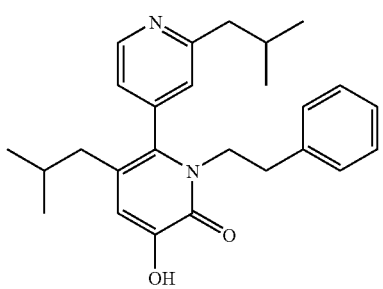

3-Hydroxy-5-isobutyl-6-(2-isobutyl-4-pyridyl)-1-(2-phenylethyl)-1H-pyridin-2-one (3)

$^1$H NMR (500 MHz, CDCl$_3$): δ 0.73 (d, J=6.5 Hz, 3H), 0.74 (d, J=6.5 Hz, 3H), 0.92 (d, J=6.5 Hz, 3H), 0.94 (d, J=6.5 Hz, 3H), 1.63 (m, 1H), 1.88 (m, 2H), 2.04 (m, 1H), 2.66-2.73 (m, 2H), 2.88 (m, 2H), 3.95 (t, J=8.0 Hz, 2H), 6.74-6.84 (m, 5H), 7.19 (m, 2H), 8.63 (d, J=5.0 Hz, 1H); $^{13}$C NMR (125 MHz, CDCl$_3$): δ 22.1, 22.2, 22.3, 22.5, 29.2, 29.4, 34.3, 40.4, 47.4, 48.6, 115.9, 118.4, 122.6, 125.1, 126.7, 128.6, 128.8, 133.3, 137.8, 142.1, 145.5, 149.6, 157.9, 162.5; HRMS-EI (m/z): [M+H$^+$] calcd for [C$_{26}$H$_{33}$N$_2$O$_2$]$^+$, 405.2542. found 405.2550.

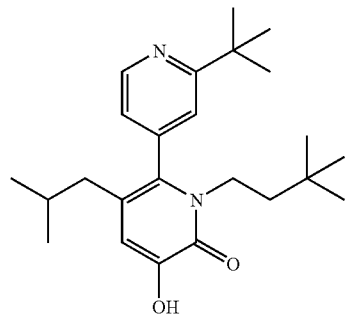

6-(2-tert-Butyl-4-pyridyl)-3-hydroxy-5-isobutyl-1-(3,3-dimethylbutyl)1H-pyridin-2-one (5)

$^1$H NMR (500 MHz, CDCl$_3$): δ (s, 9H), 0.66 (d, J=7.0 Hz, 3H), 0.68 (d, J=7.0 Hz, 3H), 1.31-1.43 (m, 11H), 1.58 (m, 1H), 1.81 (m, 2H), 3.61 (m, 1H), 3.82 (m, 1H), 6.70 (s, 1H), 6.93 (dd, J=5.0 Hz, J$_2$=1.0 Hz, 1H), 7.16 (m, 1H), 8.61 (d, 5.0 Hz, 1H); $^{13}$C NMR (125 MHz, CDCl$_3$): δ 22.0, 22.1, 28.6, 29.1, 29.5, 29.9, 37.4, 40.2, 41.4, 43.5, 115.9, 118.4, 121.1, 122.2, 133.4, 141.9, 145.5, 148.8, 157.6, 169.8; HRMS-EI (m/z): [M+H$^+$] calcd for [C$_{24}$H$_{37}$N$_2$O$_2$]$^+$, 385.2855. found 385.2857.

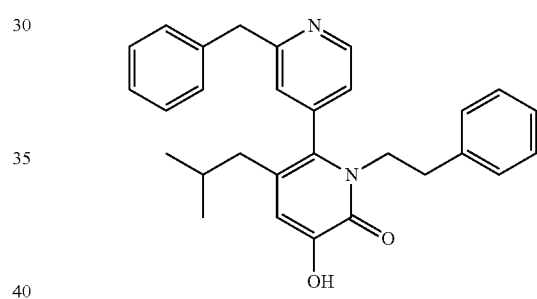

6-(2-Benzyl-4-pyridyl)-3-hydroxy-5-isobutyl-1-(2-phenylethyl)-1H-pyridin-2-one (6)

$^1$H N (400 MHz, CDCl$_3$): δ 0.63 (d, J=6.8 Hz, 3H), 0.69 (d, J=6.8 Hz, 3H), 1.55 (m, 1H), 1.76-1.83 (m, 2H), 2.81 (m, 2H), 3.87 (m, 2H), 4.21 (s, 2H), 6.77 (m, 5H), 7.17-7.26 (m, 9H), 8.64 (d, J=4.8 Hz, 1H); $^{13}$C NMR (100 MHz, CDCl$_3$): δ 22.1, 22.2, 29.1, 34.3, 40.3, 44.5, 48.6, 116.1, 118.5, 122.9, 124.9, 126.6, 126.7, 128.6, 128.7, 128.8, 128.9, 133.1, 137.7, 138.8, 142.6, 145.6, 149.6, 157.8, 161.9; HRMS-EI (m/z): [M+H$^+$] calcd for [C$_{29}$H$_{31}$N$_2$O$_2$]$^+$, 439.2386. found 439.2391.

3-hydroxy-5-isobutyl-6-(2-isobutyl-4-pyridyl)-1-(3,3-dimethylbutyl)1H-pyridin-2-one (4)

$^1$H NMR (500 MHz, CDCl$_3$): δ 0.63 (s, 9H), 0.68 (d, J=7 Hz, 6H), 0.86 (d, J=6.0 Hz, 3H), 0.89 (d, J=6.0 Hz, 3H), 1.31 (m, 2H), 1.58 (m, 1H), 1.82 (m, 2H), 2.08 (m, 1H), 2.66 (m, 2H), 3.71 (m, 2H), 6.69 (s, 1H), 6.96 (m, 2H), 8.60 (d, J=5 Hz, 1H); $^{13}$C NMR (125 MHz, CDCl$_3$): δ 22.0, 22.1, 22.2, 22.4, 28.7, 29.1, 29.3, 29.7, 40.3, 41.5, 43.7, 47.4, 115.5, 118.4, 122.6, 125.2, 133.1, 142.0, 145.4, 149.5, 157.3, 162.4; HRMS-EI (m/z): [M+H$^+$] calcd for [C$_{24}$H$_{36}$N$_2$O$_2$]$^+$, 384.2777. found 384.2780.

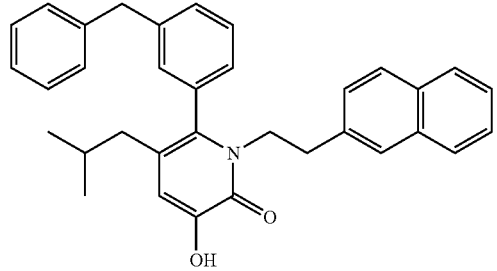

6-(2-Benzyl-4-pyridyl)-3-hydroxy-5-isobutyl-1-(2-(2-naphthyl)ethyl)-1H-pyridin-2-one (7) (TFA salt)

$^1$H NMR (500 MHz, CDCl$_3$): δ0.46 (d, J=6.5 Hz, 3H), 0.55 (d, J=6.5 Hz, 3H), 1.40 (m, 1H), 1.49 (m, 1H), 1.65 (m, 1H), 2.98-3.10 (m, 2H), 3.75 (d, J=15.0 Hz, 1H), 3.85 (m, 1H), 4.14 (m, 1H), 4.23 (d, J=15.0 Hz, 1H), 6.36 (s, 1H), 6.78 (s, 1H), 6.82 (m, 2H), 6.98 (m, 2H), 7.18-7.26 (m, 4H), 7.51 (m, 2H), 7.69 (m, 2H), 7.87 (m, 1H), 8.63 (d, J=5.5 Hz, 1H); $^{13}$C NMR (125 MHz, CDCl$_3$): δ 21.8, 22.0, 29.0, 34.0, 40.1, 40.6, 49.0, 115.7, 119.2, 125.9, 126.3, 126.7, 127.3, 127.5, 127.6, 127.7, 128.4, 128.8, 129.2, 131.2, 132.3, 133.5, 135.1, 136.0, 144.2, 146.2, 147.7, 157.8, 159.0; HRMS-EI (m/z): [M+H$^+$] calcd for [C$_{33}$H$_{33}$N$_2$O$_2$]$^+$, 489.2542. found 489.2591.

Fluorescence Polarization Assay:

A master solution in assay buffer (20 mM HEPES, pH 7.5; 0.005% Nonidet P-40; 10 mM DTT) was prepared containing ERα (150 nM), 17β-estradiol (4 μM) and fluorescently labeled D22 (2 nM). A stock solution of the inhibitor in DMSO was used to prepare a solution of the inhibitor in assay buffer. The inhibitor was serially diluted (2-fold dilutions) into buffer in a 384-well plate to a volume of 20 μL in each well. To these wells 20 μL of the master solution were added to obtain a final volume of 40 μL with the following final concentrations: ERα 75 nM, 17β-estradiol 2 μM and D22 1 nM in addition to the corresponding inhibitor concentration. The plate was incubated for 4 h at RT in the dark and polarization values were measured. Pure buffer was used as the background signal. A well with only D22 and buffer and another with D22, ERα and 17β-estradiol were used as controls for minimum and maximum polarization respectively. Regression analyses were carried out using SigmaPlot 2004 (Systat Co.) ligand binding macro module. Experimental binding was fitted either to sigmoidal dose-respond (variable slope curve) or to one site competition curve. The K$_i$ values were obtained from the IC$_{50}$ by using a K$_d$ value of 31 nM for the fluorescent peptide (D22) at a concentration of 1 nM. See, Ozers, et al., *Molecular Endocrinology*, 2005, 19(1), 25-34.

To validate the assay the inventors performed a competition experiment using a control peptide with the sequence CLTERHKILHRLLQE (SRC-1 NR). This peptide mirrors the second NR box of the coactivator protein SRC-1 and binds in the coactivator binding site on the ER surface. Titration of a solution of ERα, D22 and saturating concentration of 17β-estradiol showed the expected decrease of polarization at increasing peptide concentration indicative of the control peptide displacing D22 from the binding site. The K$_i$ value obtained for the control peptide was 0.95 μM which is comparable with the reported value of 1 μM. See, Rodriguez, et al., *Journal of Medicinal Chemistry*, 2004, 47, 600-611 and Tamrazi, et al., *Molecular Endocrinology*, 2002, 16, 27062719.

Figure 2:
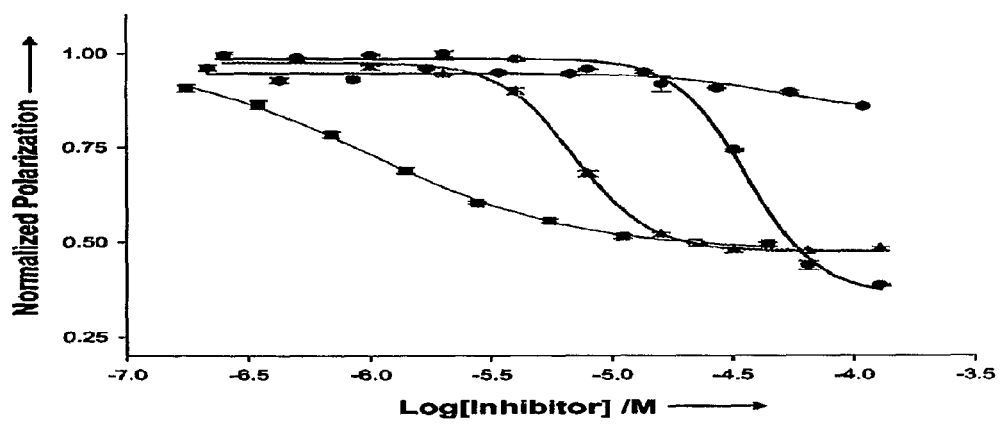
FIG. 2 shows the result of a fluorescence polarization titration for several compounds which appear in FIG. 1. Titration curves for compounds 1 (●) which slopes rapidly downward, 5 (●) which stays relatively constant at about 0.95, 6 (▲) and control peptide SRC-1 NR II (■).

A number of compounds were measured using the fluorescence polarization assay and the results are presented in FIG. 2 and FIGS. 7 and 8 to provide Ki values for the various compounds in μM.

Radioligand Assay

The radioligand assay to determine the affinity for the estradiol binding site was carried out by MDS Pharma Services using [$^3$H]estradiol and ERα from human recombinant insect Sf9 cells. See, Obourn, et al., *Biochemistry*, 1993, 32, 6229.

Procedure: Ammonium sulfate precipitates of the hER were dissolved in TDEE buffer containing 100 mM KCl, 0.5 mM leupeptin, and 10% glycerol. G-Globulin was added to give a final protein concentration of 1.5 mg/mL. The hER was incubated with a varied concentration of [$^3$H]estradiol, and the nonspecific binding was measured by a parallel incubation with [$^3$H]estradiol plus a 300-fold excess of estradiol for 15 h at 4° C. At the completion of the incubation, 50 μL of each mixture was removed and the total [$^3$H]estradiol concentration determined. Then 100 μL of a 50% slurry of hydroxylapatite (in 40 mM Tris, pH 7.4, 1 mM EDTA, 1 mM EGTA) was added and allowed to bind hER for 40 min. The hydroxylapatite was washed three times with 0.5 mL of 40 mM Tris, pH 7.4, 1 mM EDTA, 1 mM EGTA and 100 mM KCl. The hydroxylapatite pellets were suspended in 1 mL of ethanol and counted in 5 mL of scintillation fluid, and the receptor-bound [$^3$H]estradiol was measured. Each value was the mean of three determinations.

References:

[1] J. E. Darnell, Nature Rev. *Cancer* 2002, 2, 740-749.

[2] B. R. Henke, D. Heyer, *Curr. Opin. Drug Discovery Dev.* 2005, 8, 437-448.

[3] a) A. L. Rodriguez, A. Tamrazi, M. L. Collins, J. A. Katzenellenbogen, *J. Med. Chem.* 2004, 47, 600-611; b) D. L. Shao, T. J. Berrodin, E. Manas, D. Hauze, R. Powers, A. Bapat, D. I. Gonder, R. C. Winneker, D. E. Frail, *J. Steroid Biochem. Mol. Biol.* 2004, 88, 351-360; c) L. A. Arnold, E. Estébanez-Perpiñá, M. Togashi, N. Jouravel, A. Shelat, A. C. McReynolds, E. Mar, P. Nguye, J. D. Baxter, R. J. Fletterick, P. Webb, R. K. Guy, *J. Bio. Chem.* 2005, 280, 43048-43055.

[4] A. K. Shiau, D. Barstad, P. M. Loria, L. Cheng, P. J. Kushner, D. A. Agard, G. L. Greene, *Cell* 1998, 95, 927-937; b) *Protein Data Base ID:* 3erd; b) FIG. 1a was generated using PyMol software. Delano, San Carlos, Calif., USA.

[5] a) D. M. Heery, E. Kalkboven, S. Hoare, M. G. Parker, *Nature* 1997, 387, 733-736; b) C. Y. Chang, J. D. Norris, H. Gron, L. A. Paige, P. T. Hamilton, D. J. Kenan, D. Fowlkes, D. P. McDonnell, *Mol. Cell. Biol.* 1999, 19, 8226-8239.

[6] a) A. M. Leduc, J. O. Trent, J. L. Wittliff, K. S. Bramlett, S. L. Briggs, N. Y. Chirgadze, Y. Wang, T. P. Burris, A. F. Spatola, *Proc. Natl. Acad. Sci. USA* 2003, 100, 11273-11278; b) T. R. Geistlinger, R. K. Guy, *J. Am. Chem. Soc.* 2003, 125, 6852-6853; c) A. K. Galande, K. S. Bramlett, J. O. Trent, T. P. Burris, J. L. Wittliff, A. F. Spatola, *Chem Bio Chem* 2005, 6, 1991-1998; d) T. R. Geistlinger, A. C. McReynolds, R. K. Guy, *Chem. Biol.* 2004, 11, 273-281.

[7] a) B. P. Orner, J. T. Ernst, A. D. Hamilton, *J. Am. Chem. Soc.* 2001, 123, 5382-5383; b) J. T. Ernst, J. Becerril, H. S. Park, H. Yin, A. D. Hamilton, *Angew. Chem.* 2003, 115, 553-557; *Angew. Chem. Int. Ed.* 2003, 42, 535-539; c) H. Yin, A. D. Hamilton, *Bioorg. Med. Chem. Lett.* 2004, 14, 1375-1379.

[8] a) O. Kutzki, H. S. Park, J. T. Ernst, B. P. Orner, H. Yin, A. D. Hamilton, *J. Am. Chem. Soc.* 2002, 124, 11838-11839; b) H. Yin, G. I. Lee, H. S. Park, G. A. Payne, J. M. Rodriguez, S. M. Sebti, A. D. Hamilton, *Angew. Chem.* 2005, 117, 2764-2767; *Angew. Chem. Int. Ed.* 2005, 44, 2704-2707.

[9] a) E. Jacoby, *Bioorg. Med. Chem. Lett.* 2002, 12, 891-893; b) I. C. Kim, A. D. Hamilton, *Org. Lett.* 2006, 8, 1751-1754; c) D. C. Horwell, W. Howson, W. P. Nolan, G. S. Ratcliffe, D. C. Rees, H. M. G. Willems, *Tetrahedron* 1995, 51, 203-216.

[10] F. Fontana, F. Minisci, M. C. N. Barbosa, E. Vismara, *Tetrahedron* 1990, 46, 2525-2538.

[11] I. Collins et al. *J. Med. Chem.* 2002, 45, 1887-1900. See Supporting Information.

[12] A. Tamrazi, K. E. Carlson, J. R. Daniels, K. M. Hurth, J. A. Katzenellenbogen, *Mol. Endocrinol.* 2002, 16, 2706-2719.

The invention claimed is:
1. The compound:

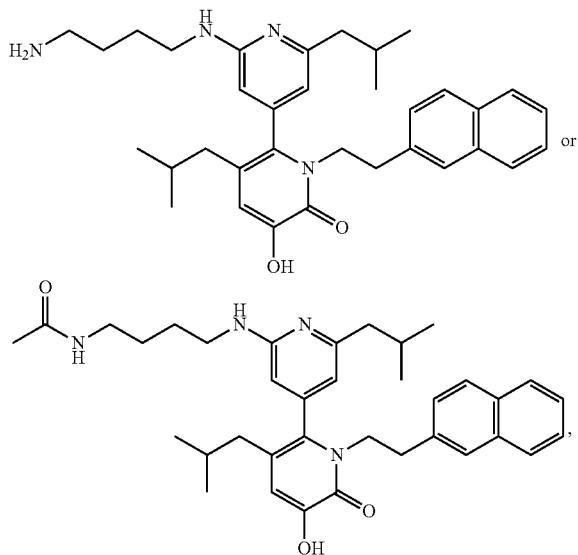

or pharmaceutically acceptable salt thereof.

2. A compound according to the chemical structure:

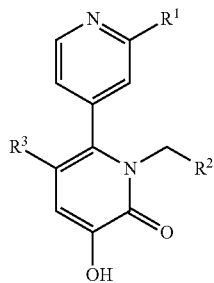

Where $R^1$ is an isopropyl group, an isobutyl group, a tert-butyl group or a benzyl group, $R^2$ is an isopropyl group, an isobutyl group, an isopropenyl group, a 2,2,-dimethyl propyl group, a benzyl group, a —CH$_2$(2-naphthyl) group or a —CH$_2$(1-naphthyl) group; and $R^3$ is an isopropyl group, an iso-butyl group, a neopentyl group, a benzyl group, a —CH$_2$CH$_2$(2-naphthyl) group or a —CH$_2$CH$_2$(1-naphthyl) group, or a pharmaceutically acceptable salt thereof.

3. The compound according to claim 2 wherein $R^1$ is an isopropyl group or a benzyl group.

4. The compound according to claim 2 wherein $R^1$ is a benzyl group.

5. The compound according to claim 2 wherein $R^2$ is an isopropyl group, an isobutyl group, a benzyl group, a —CH$_2$(2-naphthyl) group or a —CH$_2$(1-naphthyl) group.

6. The compound according to claim 5 wherein $R^2$ is a benzyl group, a —CH$_2$(2-naphthyl) group or a —CH$_2$(1-naphthyl) group.

7. The compound according to claim 2 wherein $R^3$ is an isobutyl group, a neo-pentyl group, a benzyl group, a —CH$_2$CH$_2$(2-naphthyl) group or a —CH$_2$CH$_2$(1-naphthyl) group.

8. The compound according to claim 2 wherein $R^1$ is an isopropyl group or a benzyl group, $R^2$ is an isopropyl group, an isobutyl group, a benzyl group, a —CH$_2$(2-naphthyl) group or a —CH$_2$(1-naphthyl) group and $R^3$ is an isobutyl group, a benzyl group, a —CH$_2$CH$_2$(2-naphthyl) group or a —CH$_2$CH$_2$(1-naphthyl) group.

9. A pharmaceutical composition comprising an effective amount of a compound according to claim 2 in combination with a pharmaceutically acceptable carrier, additive or excipient.

10. A pharmaceutical composition comprising an effective amount of a compound according to claim 3 in combination with a pharmaceutically acceptable carrier, additive or excipient.

11. A pharmaceutical composition comprising an effective amount of a compound according to claim 4 in combination with a pharmaceutically acceptable carrier, additive or excipient.

12. A pharmaceutical composition comprising an effective amount of a compound according to claim 5 in combination with a pharmaceutically acceptable carrier, additive or excipient.

13. A pharmaceutical composition comprising an effective amount of a compound according to claim 6 in combination with a pharmaceutically acceptable carrier, additive or excipient.

14. A pharmaceutical composition comprising an effective amount of a compound according to claim 7 in combination with a pharmaceutically acceptable carrier, additive or excipient.

15. A pharmaceutical composition comprising an effective amount of a compound according to claim 8 in combination with a pharmaceutically acceptable carrier, additive or excipient.

16. The composition according to claim 9 in oral dosage form.

17. The composition according to claim 15 in oral dosage form.

18. A method of treating breast cancer in a patient in need comprising administering to said patient a composition according to claim 2.

19. A method of treating breast cancer in a patient in need comprising administering to said patient a composition according to claim 3.

20. A method of treating breast cancer in a patient in need comprising administering to said patient a composition according to claim 4.

21. A method of treating breast cancer in a patient in need comprising administering to said patient a composition according to claim 5.

22. A method of treating breast cancer in a patient in need comprising administering to said patient a composition according to claim 6.

23. A method of treating breast cancer in a patient in need comprising administering to said patient a composition according to claim 7.

24. A method of treating breast cancer in a patient in need comprising administering to said patient a composition according to claim 8.

* * * * *